United States Patent
Zheng et al.

(10) Patent No.: US 10,351,578 B2
(45) Date of Patent: Jul. 16, 2019

(54) HETEROCYCLIC-SUBSTITUTED PYRIDINOPYRIMIDINONE DERIVATIVE AS CDK INHIBITOR AND USE THEREOF

(71) Applicant: Shanghai Xunhe Pharmaceutical Technology Co. Ltd., Shanghai (CN)

(72) Inventors: Yongyong Zheng, Shanghai (CN); Hua Jin, Shanghai (CN); Feng Zhou, Shanghai (CN); Meihua Huang, Shanghai (CN); Xin Meng, Beijing (CN)

(73) Assignee: Shanghai Xunhe Pharmaceutical Technology Co. Ltd., Shanghai (CN)

( * ) Notice: Subject to any disclaimer, the term of this patent is extended or adjusted under 35 U.S.C. 154(b) by 0 days.

(21) Appl. No.: 16/155,867

(22) Filed: Oct. 9, 2018

(65) Prior Publication Data
US 2019/0071453 A1    Mar. 7, 2019

Related U.S. Application Data

(63) Continuation of application No. PCT/CN2017/078935, filed on Mar. 31, 2017.

(30) Foreign Application Priority Data

Apr. 11, 2016    (CN) .......................... 2016 1 0220275

(51) Int. Cl.
| C07D 498/04 | (2006.01) |
| C07D 498/10 | (2006.01) |
| C07D 513/04 | (2006.01) |
| A61P 35/00  | (2006.01) |

(52) U.S. Cl.
CPC ............. *C07D 498/04* (2013.01); *A61P 35/00* (2018.01); *C07D 498/10* (2013.01); *C07D 513/04* (2013.01)

(58) Field of Classification Search
CPC ..................................................... C07D 498/04
USPC ........................................................ 514/222.5
See application file for complete search history.

(56) References Cited

PUBLICATIONS

Choi YJ and Anders L, Oncogene 33:1890-903, 2014.*

* cited by examiner

*Primary Examiner* — Kahsay Habte

(57) ABSTRACT

The present invention relates to a heterocyclic-substituted pyridinopyrimidinone derivative and the use thereof as a therapeutically effective cyclin-dependent kinase (CDK) inhibitor. In particular, the present invention relates to the use of a new heterocyclic-substitute pyridinopyrimidinone derivative as shown in formula (I) and a pharmaceutical composition thereof as a selective CDK4/6 inhibitor in preventing or treating diseases related to CDK4/6.

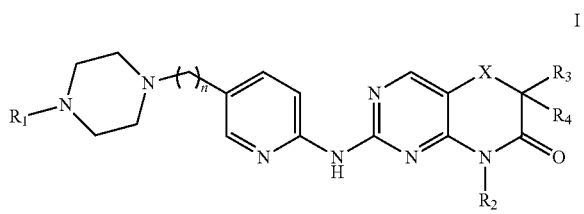

5 Claims, No Drawings

HETEROCYCLIC-SUBSTITUTED PYRIDINOPYRIMIDINONE DERIVATIVE AS CDK INHIBITOR AND USE THEREOF

CROSS-REFERENCE TO RELATED APPLICATION

The present application is a continuation of international application No. PCT/CN2017/078935 filed on Mar. 31, 2017, which claims priority of Chinese patent application No. CN201610220275.5, filed on Apr. 11, 2016, which are hereby incorporated by reference in their entireties.

TECHNICAL FIELD

The disclosure relates to the technical field of pharmaceutical preparation, in particular to a heterocyclic-substituted pyridinopyrimidinone as CDK inhibitor and use thereof.

BACKGROUND

Cyclin-dependent kinase (CDK) and cyclin are important factors in the regulation of cell cycle. CDK can form a heterodimer with cyclin, wherein CDK is a catalytic subunit, cyclin is a regulatory subunit, and various cyclin-CDK complexes are formed, which phosphorylate different substrates, thereby promoting and transforming the different phases of a cell cycle.

There are at least 9 CDKs in mammals. The transition from G1 phase to S phase in cells is mainly controlled by G1 phase CDK kinase. CDK kinases that bind to G1 cyclins mainly comprise CDK2, CDK4, and CKD6. Cyclin D mainly binds to CDK4 and CKD6 and regulates the activity of the latter; cyclin E binds to CDK2 at G1/S phase, exhibiting CDK2 kinase activity and promoting cell's entry into S phase. G2/M phase is mainly regulated by CDK1 kinase, Cyclin A and CyclinB binds to CDK1, and CDK1 phosphorylates the substrate protein, such as histone H1 for chromosome condensation, or laminin for disintegration of nuclear membrane. During M phase, APC, an anaphase-promoting complex that is activated by M-promoting factor (MPF), is ubiquitously linked to Cyclin A and Cyclin B. Through polyubiquitylation, they are degraded by a proteasome, which completes a cell cycle (Malumbres M. et al. Nat Cell Biol 11:1275, 2009; Malumbres M. et al. Nat Rev Cancer 9:153, 2009).

In the past decade, CDK inhibitors have been regarded as a hot spot for developing new anti-tumor drug in the global pharmaceutical industry, and more than 20 CDK inhibitors have entered clinical development. Although CDK inhibitors had significant preclinical anti-tumor pharmacodynamics, the results of most previous clinical trials were unsatisfactory. The main problems include lack of efficacy and toxicity in solid tumors (Guha M. Nat Rev Drug Dis 11:892, 2012). During the analysis of serious toxic side effects, it was found that some CDK inhibitor drugs lack selectivity for CDK subtypes, resulting in greater side effects.

CDK4 and CDK6 are two closely related kinases that bind to Cyclin D during the tumor cell cycle and cause transition of G1 phase to S phase, which is essential for the cell cycle progression of DNA replication for cell division. Changes in the G1-S phase transition control mechanism through various genetic and biochemical adaptations have been found in more than 90% of human tumors. P16 and human retinoblastoma (Rb) are important tumorsuppressor proteins that regulate cell cycle. P16 gene protein inhibits the feedback loop of CDK4, Cyclin D1 and Rb, and prevents the cell from hyperproliferation by regulating the protein activity of Rb for tumor suppression. It has been shown that activation of CDK4 and CDK6 causes changes in cell cycle in human tumors (such as breast tumor and myeloma). Inhibition of CDK4 and CDK6 can prevent inactivation of tumor suppressor protein Rb and interfere with tumor cell cycle progression (Choi Y J and Anders L, Oncogene 33:1890-903, 2014).

CDK4/6 plays a key role in the dysregulation of cell cycle control in various solid tumors and hematological tumors. There are several selective CDK4/6 inhibitors in clinical stages at present (e.g., Palbociclib, LY2835219, and LEE011). The clinical evaluation of these drugs also includes metastatic breast cancer, ovarian cancer, liposarcoma, non-small cell lung cancer, liver cancer, glioblastoma, melanoma, multiple myeloma and lymphoma.

Although many CDK inhibitor compounds have been disclosed, a variety of drugs, particularly CDK4/6 inhibitors for treating CDK-related disorders are still needed due to CDK-mediated pathology.

SUMMARY

One of the objects of the present disclosure is to provide a novel heterocyclic-substituted pyridinopyrimidinone or a pharmaceutically acceptable salt thereof.

The second object of the present disclosure is to provide use of the compound as a novel CDK4/6 inhibitor in the preparation of a medicament for the prevention or treatment of CDK4/6-related diseases. The CDK4/6-related diseases caused by the imbalance of the cycle control involved with CDK4/6, especially malignant tumors to be treated include but not limited to breast cancer, ovarian cancer, prostate cancer, colorectal cancer, pancreatic cancer, liver cancer, melanoma, gastric cancer, and solid tumors.

For above object, the present disclosure provides a heterocyclic-substituted pyridinopyrimidinone represented by the following Formula I or a pharmaceutically acceptable Salt thereof:

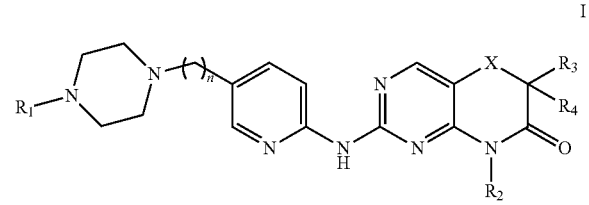

I wherein,
$R_1$ represents hydrogen, $C_1$-$C_3$ alkyl, or $C_3$-$C_7$ cycloalkyl;
$R_2$ represents $C_1$-$C_5$ alkyl, $C_3$-$C_7$ cycloalkyl, 5-6 membered heteroaryl, phenyl, or substituted phenyl;
$R_3$ and $R_4$ independently represents hydrogen, $C_1$-$C_3$ alkyl, $C_3$-$C_7$ cycloalkyl, acetyl, halogen, trifluoromethyl, cyano or $CONR_5R_6$;
or $R_3$, $R_4$ together with the carbon atom to which they are attached form a $C_3$-$C_7$ aliphatic ring;
$R_5$ and $R_6$ independently represents hydrogen or methyl;
X represents O, or S;
n is 0 or 1.

The present disclosure also provides a pharmaceutical composition comprising at least one pharmaceutically acceptable carrier, and at least one compound of Formula (I)

described herein and a pharmaceutically acceptable salt thereof as a CDK4/6 inhibitor.

As used herein, "$C_1$-$C_3$ alkyl" refers to methyl, ethyl, n-propyl, or iso-propyl; "$C_1$-$C_5$ alkyl" refers to methyl, ethyl, n-propyl, iso-propyl, n-butyl, iso-butyl, sec-butyl, tert-butyl, 1-pentyl, 2-pentyl, 3-pentyl, 2-methyl-3-butyl, 1,1-dimethyl-1-propyl, 2,2-dimethyl-1-propyl; "$C_1$-$C_3$alkoxy" refers to methoxy, ethoxy, n-propoxy, iso-propoxy; "halogen" refers to F, Cl, Br, I; "$C_3$-$C_7$ cycloalkyl" refers to cyclopropyl, cyclobutyl, cyclopentyl, cyclohexyl, cycloheptyl; and "5-6 membered heteroaryl" refers to a 5-6 membered aromatic monocyclic ring containing 1-3 heteroatoms selected from N, O, S, and the remaining ring atoms are carbon.

Typical compounds of the present disclosure include but not limited to those in following Table 1:

TABLE 1

| Compound | Structure |
|---|---|
| I-1 | 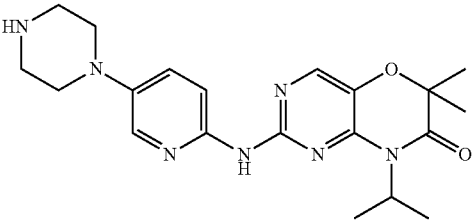 [SMILES: CC(C)N1C(=O)C(C)(C)Oc2cnc(Nc3ccc(N4CCNCC4)cn3)nc21] |
| I-2 | 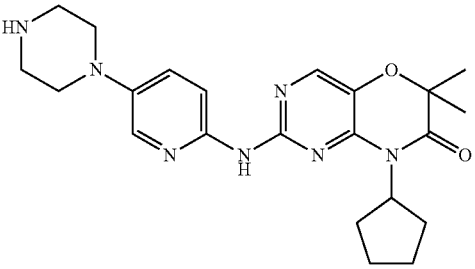 [SMILES: CC1(C)Oc2cnc(Nc3ccc(N4CCNCC4)cn3)nc2N(C2CCCC2)C1=O] |
| I-3 | 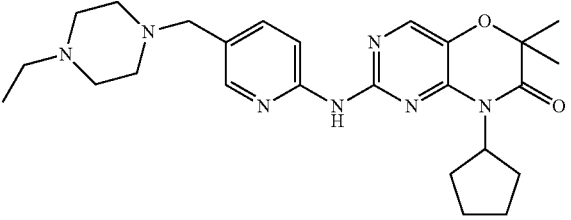 [SMILES: CCN1CCN(Cc2ccc(Nc3ncc4c(n3)N(C3CCCC3)C(=O)C(C)(C)O4)nc2)CC1] |
| I-4 | 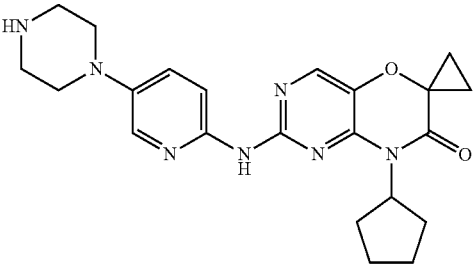 [SMILES: O=C1N(C2CCCC2)c2nc(Nc3ccc(N4CCNCC4)cn3)ncc2OC12CC2] |
| I-5 | 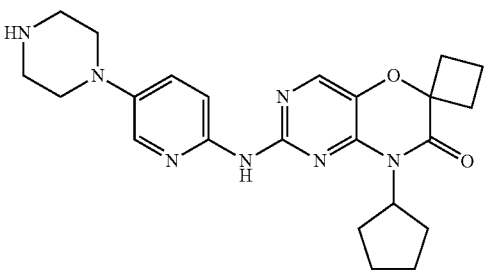 [SMILES: O=C1N(C2CCCC2)c2nc(Nc3ccc(N4CCNCC4)cn3)ncc2OC12CCC2] |

TABLE 1-continued

| Compound | Structure |
|---|---|
| I-6 | 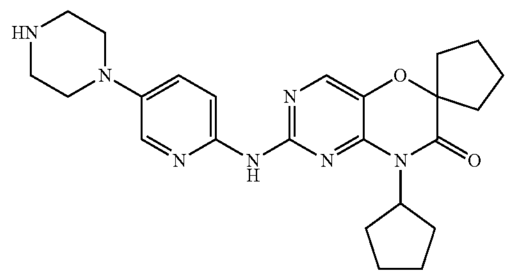 [SMILES: O=C1N(C2CCCC2)c2nc(Nc3ccc(N4CCNCC4)cn3)ncc2OC12CCCC2] |
| I-7 | 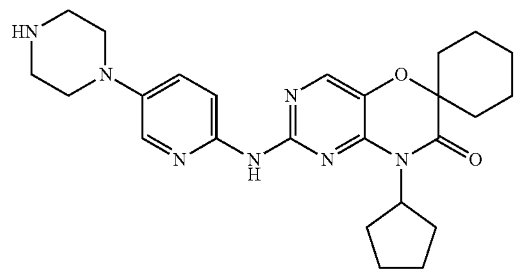 [SMILES: O=C1N(C2CCCC2)c2nc(Nc3ccc(N4CCNCC4)cn3)ncc2OC12CCCCC2] |
| I-8 | 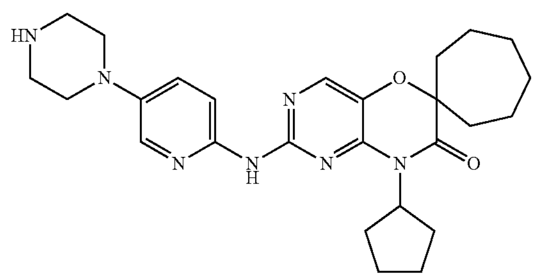 [SMILES: O=C1N(C2CCCC2)c2nc(Nc3ccc(N4CCNCC4)cn3)ncc2OC12CCCCCC2] |
| I-9 | 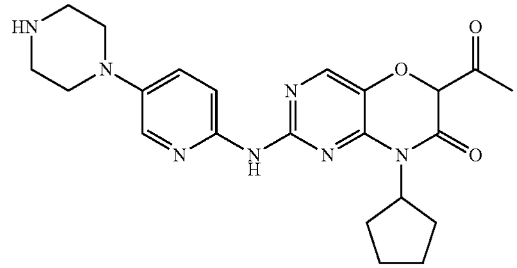 [SMILES: CC(=O)C1Oc2cnc(Nc3ccc(N4CCNCC4)cn3)nc2N(C2CCCC2)C1=O] |
| I-10 | 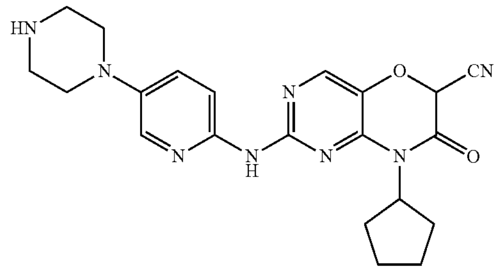 [SMILES: N#CC1Oc2cnc(Nc3ccc(N4CCNCC4)cn3)nc2N(C2CCCC2)C1=O] |

TABLE 1-continued
| Compound | Structure |
|---|---|
| I-11 | 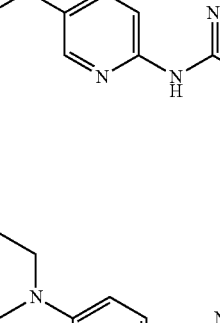 |
| I-12 | 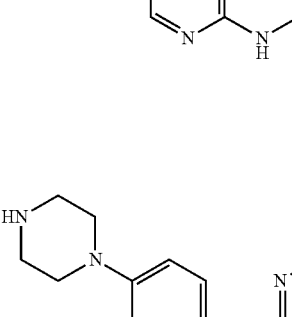 |
| I-13 | 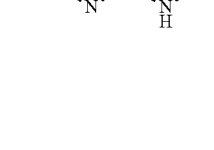 |
| I-14 | 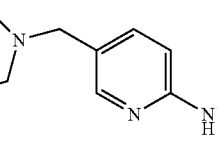 |
| I-15 | 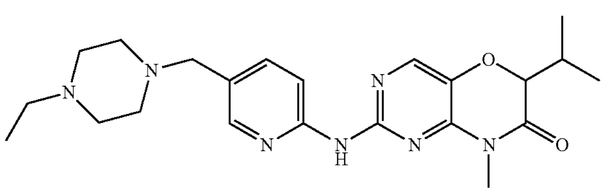 [SMILES: CCN1CCN(Cc2ccc(Nc3ncc4c(n3)N(C)C(=O)C(C(C)C)O4)nc2)CC1] |
| I-16 | 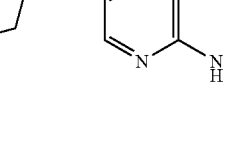 |

TABLE 1-continued

| Compound | Structure |
|---|---|
| I-17 | 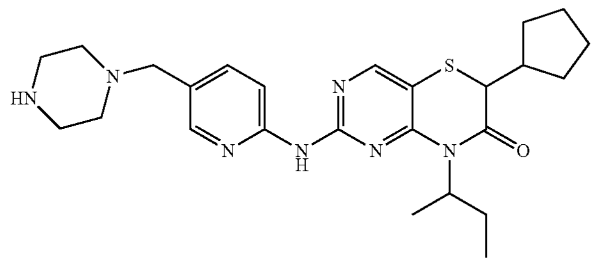 [SMILES: CCC(C)N1C(=O)C(C2CCCC2)Sc2cnc(Nc3ccc(CN4CCNCC4)cn3)nc21] |
| I-18 | 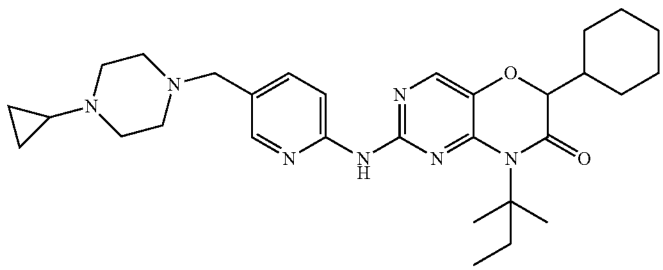 [SMILES: CCC(C)(C)N1C(=O)C(C2CCCCC2)Oc2cnc(Nc3ccc(CN4CCN(C5CC5)CC4)cn3)nc21] |
| I-19 | 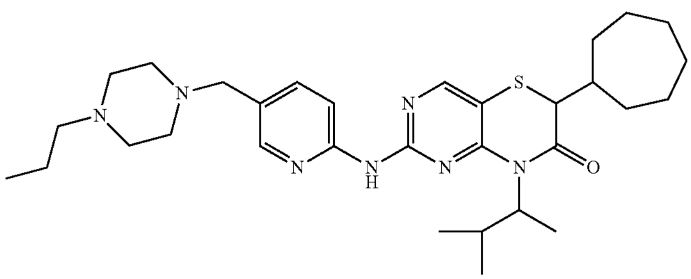 [SMILES: CCCN1CCN(Cc2ccc(Nc3ncc4c(n3)N(C(C)C(C)C)C(=O)C(C3CCCCCC3)S4)nc2)CC1] |
| I-20 | 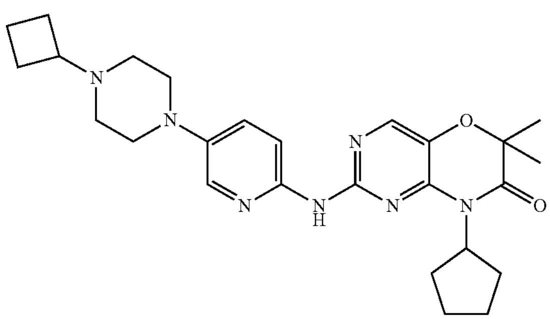 [SMILES: CC1(C)Oc2cnc(Nc3ccc(N4CCN(C5CCC5)CC4)cn3)nc2N(C2CCCC2)C1=O] |
| I-21 | 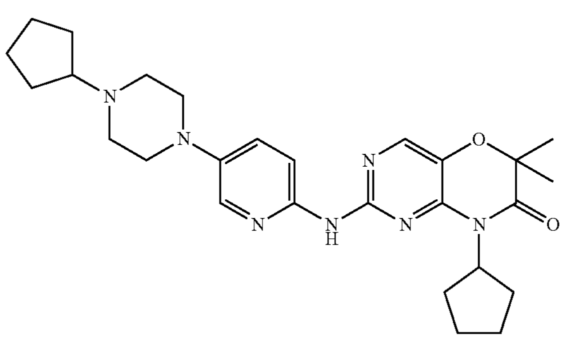 [SMILES: CC1(C)Oc2cnc(Nc3ccc(N4CCN(C5CCCC5)CC4)cn3)nc2N(C2CCCC2)C1=O] |

TABLE 1-continued
| Compound | Structure |
|---|---|
| I-22 | 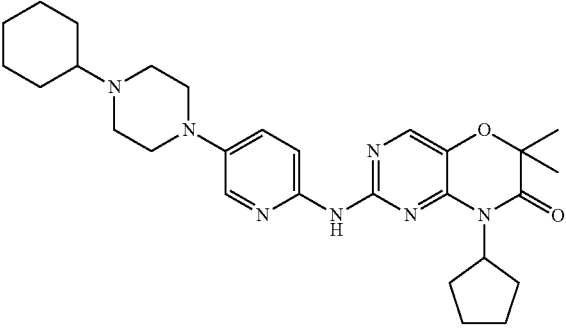 [SMILES: CC1(C)Oc2cnc(Nc3ccc(N4CCN(C5CCCCC5)CC4)cn3)nc2N(C2CCCC2)C1=O] |
| I-23 | 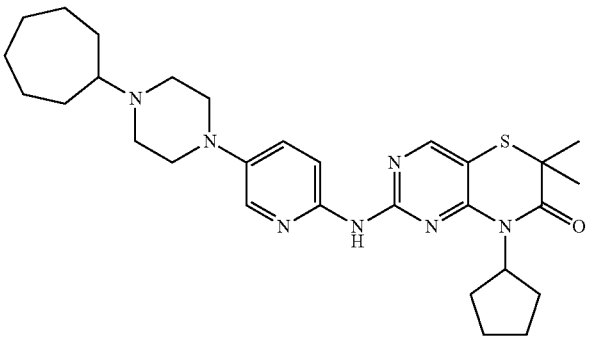 [SMILES: CC1(C)Sc2cnc(Nc3ccc(N4CCN(C5CCCCCC5)CC4)cn3)nc2N(C2CCCC2)C1=O] |
| I-24 | 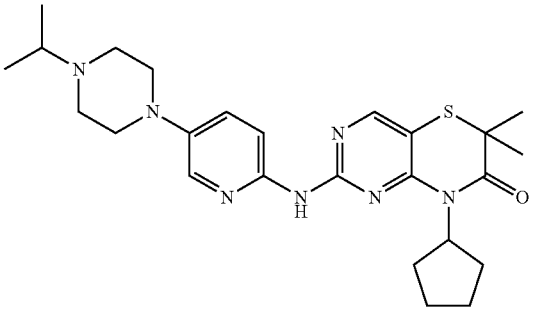 [SMILES: CC(C)N1CCN(c2ccc(Nc3ncc4c(n3)N(C3CCCC3)C(=O)C(C)(C)S4)nc2)CC1] |
| I-25 | 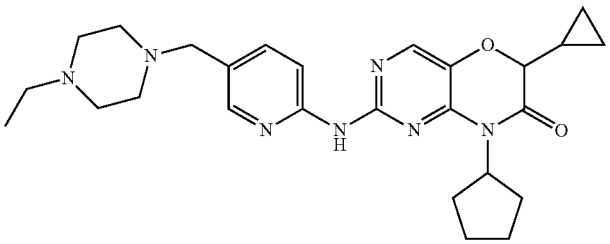 [SMILES: CCN1CCN(Cc2ccc(Nc3ncc4c(n3)N(C3CCCC3)C(=O)C(C3CC3)O4)nc2)CC1] |
| I-26 | 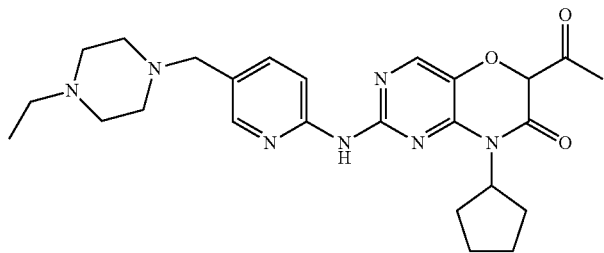 [SMILES: CCN1CCN(Cc2ccc(Nc3ncc4c(n3)N(C3CCCC3)C(=O)C(C(C)=O)O4)nc2)CC1] |

TABLE 1-continued
| Compound | Structure |
|---|---|
| I-27 | 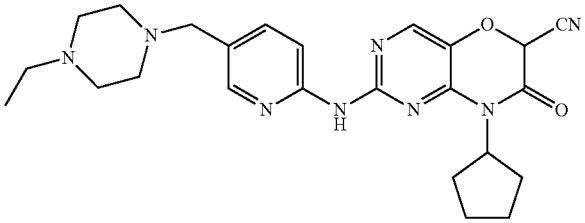 [SMILES: CCN1CCN(Cc2ccc(Nc3ncc4c(n3)N(C3CCCC3)C(=O)C(C#N)O4)nc2)CC1] |
| I-28 | 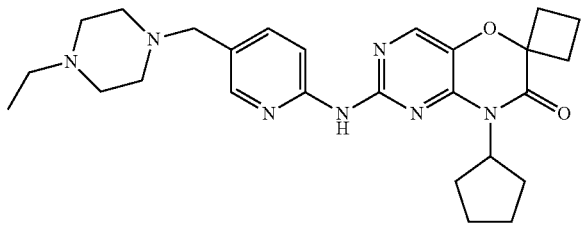 [SMILES: CCN1CCN(Cc2ccc(Nc3ncc4c(n3)N(C3CCCC3)C(=O)C3(CCC3)O4)nc2)CC1] |
| I-29 | 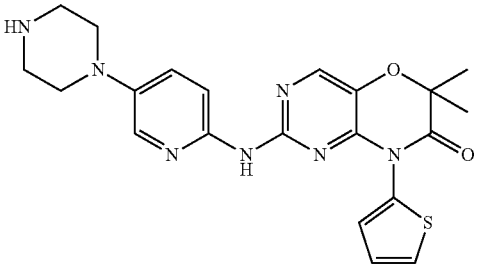 [SMILES: CC1(C)Oc2cnc(Nc3ccc(N4CCNCC4)cn3)nc2N(c2cccs2)C1=O] |
| I-30 | 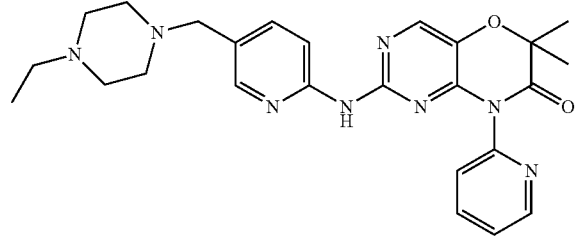 [SMILES: CCN1CCN(Cc2ccc(Nc3ncc4c(n3)N(c3ccccn3)C(=O)C(C)(C)O4)nc2)CC1] |
| I-31 | 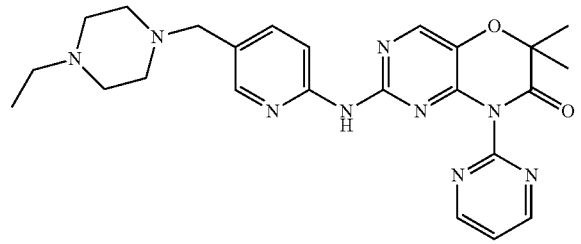 [SMILES: CCN1CCN(Cc2ccc(Nc3ncc4c(n3)N(c3ncccn3)C(=O)C(C)(C)O4)nc2)CC1] |
| I-32 | 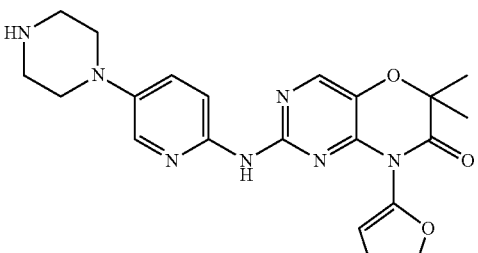 |

TABLE 1-continued
| Compound | Structure |
|---|---|
| I-33 | 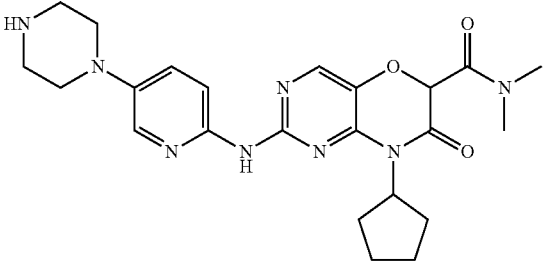 [SMILES: CN(C)C(=O)C1Oc2cnc(Nc3ccc(N4CCNCC4)cn3)nc2N(C2CCCC2)C1=O] |
| I-34 | 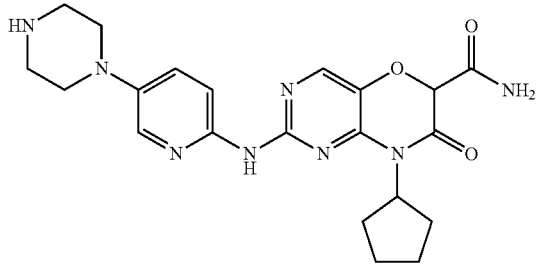 [SMILES: NC(=O)C1Oc2cnc(Nc3ccc(N4CCNCC4)cn3)nc2N(C2CCCC2)C1=O] |
| I-35 | 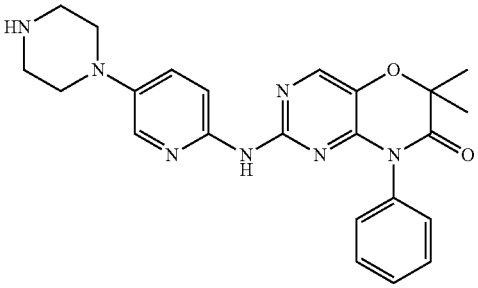 [SMILES: CC1(C)Oc2cnc(Nc3ccc(N4CCNCC4)cn3)nc2N(c2ccccc2)C1=O] |
| I-36 | 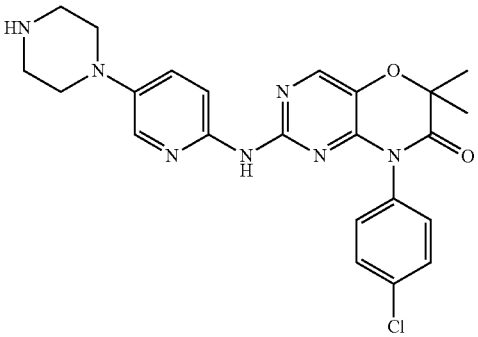 [SMILES: CC1(C)Oc2cnc(Nc3ccc(N4CCNCC4)cn3)nc2N(c2ccc(Cl)cc2)C1=O] |
| I-37 | 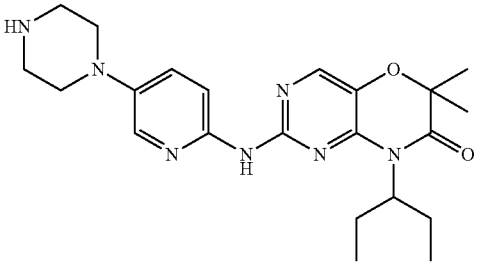 [SMILES: CCC(CC)N1C(=O)C(C)(C)Oc2cnc(Nc3ccc(N4CCNCC4)cn3)nc21] |

TABLE 1-continued

| Compound | Structure |
|---|---|
| I-38 | 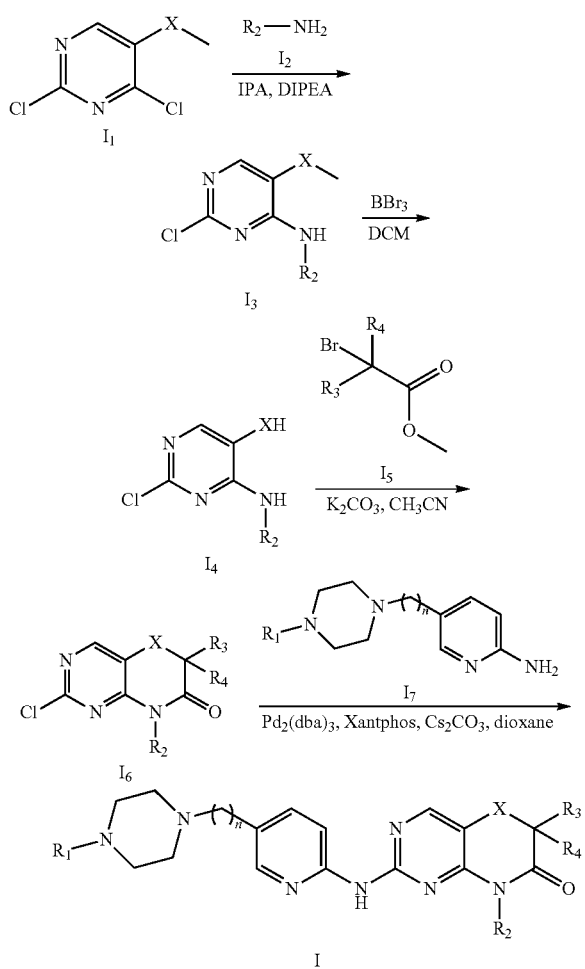 | or a pharmaceutically acceptable salt thereof.

Examples of a pharmaceutically acceptable salt include inorganic and organic salts such as hydrochloride, hydrobromide, sulfate, phosphate, citrate, tartrate, succinate, maleate, fumarate, mandelate and oxalate.

A part of the compounds of the present disclosure can be prepared by the following synthetic scheme:

$I_6$ is prepared according to the procedure reported in the literature (ISOO ITO, NORIICHI ODA, et al. Chem. Pharm. Bull., 1976, pp 1189; BURNETT DUANE A et al. WO2015066697 A1), i.e., substituted 2,4-dichloropyrimidine ($I_1$) is reacting with amine ($I_2$) under basic condition to obtain intermediate $I_3$, which is demethylated to obtain $I_4$, and $I_4$ and $I_5$ are substituted and cyclized to obtain ester intermediate $I_6$.

$I_6$ is catalytically reacted with an amine ($I_7$) to obtain the target product I.

The present disclosure relates to said heterocyclic-substituted pyridinopyrimidinone derivatives as CDK4/6 inhibitors that can be used for various clinical diseases caused by dysregulation of the cell cycle wherein CDK4/6 involves, such as cancer. Such diseases include but not limited to breast cancer, ovarian cancer, prostate cancer, colorectal cancer, liver cancer, melanoma, acute lymphocytic leukemia, chronic lymphocytic leukemia, multiple myeloma, lung cancer, gastric cancer, pancreatic cancer.

During the treatment of the disease, the derivative of the present disclosure can be used in composition to treat related cancers and other diseases by oral, injection or the like.

The composition comprises a therapeutically effective amount of a compound as described above or a pharmaceutically acceptable salt thereof and a pharmaceutically acceptable carrier.

The carrier refers to a conventional carrier in the pharmaceutical field, such as a diluent, an excipient such as water, a binder such as a cellulose derivative, gelatin, polyvinylpyrrolidone, etc.; a filler such as starch, etc.; a disintegrant such as calcium carbonate, sodium bicarbonate. Additionally, other adjuvants such as flavoring agents and sweeteners may also be added to the composition.

When used orally, they can be prepared into conventional solid preparations such as tablets, powders or capsules, etc.; when used for injection, they can be prepared as injections.

Various dosage forms of the composition of the present disclosure can be prepared with a conventional method in the medical field, wherein the content of the active ingredient is from 0.1% to 99.5% by weight.

The administration amount of the present disclosure can be varied according to the route of administration, the age, body weight of the patient, and the type and severity of the disease to be treated, and the daily dose thereof is 0.005-30 mg/kg body weight (for oral) or 0.005-30 mg/kg body weight (for injection).

The Advantageous Effect

The present disclosure provides a new heterocyclic-substituted pyridinopyrimidinone derivative or a pharmaceutically acceptable salt, which is as a CDK4/6 inhibitor in the preparation of a medicament for preventing or treating CDK4/6 related diseases, especially for the treatment of a malignant tumor, including but not limited to breast cancer, ovarian cancer, prostate cancer, colorectal cancer, liver cancer, melanoma, gastric cancer and solid tumor, and the like.

DETAILED DESCRIPTION

Embodiment of the Present Disclosure
Embodiment 1
Compound (I-1)

6,6-Dimethyl-8-isopropyl-2-(5-(1-piperazinyl)-pyridin-2-amino)-6H-pyrimido[5,4-b][1,4]oxazin-7(8H)-one Step 1: 2,4-Dichloro-5-methoxypyrimidine (1.0 g, 5.59 mmol), isopropylamine (0.33 g, 5.59 mmol), N,N-diisopropylethylamine (7.2 g, 55.9 mmol) were added to isopropanol (IPA, 10 mL) and reacted under $N_2$ protection at 100° C. for 6 h. The solvent was concentrated to dry and $H_2O$ (50 mL)/dichloromethane (DCM, 50 mL) was added into the residue and stirred for extraction. The organic layer was dried, filtered and concentrated to give 2-chloro-N-isopropyl-5-methoxypyrimidine-4-amine as a pale yellow solid (0.78 g, crude yield 69.3%).

Step 2: 2-Chloro-N-isopropyl-5-methoxypyrimidine-4-amine (0.78 g, 3.88 mmol) was added to DCM (15 mL) and BBr3 (14.5 g, 58.2 mmol) in DCM (15 mL) was added dropwise under an ice bath, and after the completion, the mixture was warmed to room temperature and stirred for 10 h. Methanol (10 mL) was added dropwise to quench the reaction. DCM (20 mL) was added to the reaction liquid, and the pH was adjusted to about 8 with a saturated $NaHCO_3$ solution. After liquid separation, the organic layer was dried, filtered and concentrated to give 2-chloro-N-isopropyl-5-hydroxypyrimidine-4-amine as a white solid (0.54 g, crude yield 74.5%).

Step 3: 2-Chloro-N-isopropyl-5-hydroxypyrimidine-4-amine (0.54 g, 2.89 mmol), methyl 2-bromoisobutyrate (0.63 g, 3.46 mmol), $K_2CO_3$ (1.2 g, 8.66 mmol) was added to acetonitrile (20 mL) and allowed to react under $N_2$ protection at 80° C. for 8 h. The solvent was concentrated to dry and $H_2O$ (50 mL)/dichloromethane (DCM, 50 mL) was added into the residue and stirred for extraction. The organic layer was dried, filtered and concentrated to give a pale yellow solid, followed by the recrystallization with ethyl acetate to give 2-chloro-6,6-dimethyl-8-isopropyl-6H-pyrimido[5,4-b][1,4]oxazin-7(8H)-one (0.73 g, yield 99.0%), MS(m/z): 257 [M+H]$^+$.

Step 4:
2-Chloro-6,6-dimethyl-8-isopropyl-6H-pyrimido[5,4-b][1,4]oxazin-7(8H)-one (0.73 g, 2.85 mmol), tert-butyl 4-(6-aminopyridin-3-yl)piperazine-1-carboxylate (0.79 g, 2.85 mmol), $Pd_2(dba)_3$ (0.26 g, 0.28 mmol), Xantphos (0.25 g, 0.43 mmol) and cesium carbonate (1.39 g, 4.28 mmol) were added to 1,4-dioxane (15 mL), and reacted under $N_2$ protection at 100° C. for 8 h. The solvent was concentrated to dry and $H_2O$ (50 mL)/dichloromethane (DCM, 50 mL) was added into the residue and stirred for extraction. The organic layer was dried, filtered and concentrated to give a pale yellow solid, followed by the anhydrous ethanol (10 mL) beating to give a pale yellow solid of 6-dimethyl-8-isopropyl-2-(5-(4-tert-butyl carboxylate-1-piperazinyl)-pyridin-2-amino)-6H-pyrimido[5,4-b][1,4]oxazin-7(8H)-one (0.50 g, yield 35.2%), MS(m/z): 498 [M+H]$^+$.

Step 5: 6,6-Dimethyl-8-isopropyl-2-(5-(4-tert-butyl carboxylate-1-piperazinyl)-pyridin-2-amino)-6H-pyrimido[5,4-b][1,4]oxazin-7(8H)-one (0.50 g, 2.0 mmol) was added to ethyl acetate (5 mL). 3N HCl-ethyl acetate solution was added under stirring and allowed to react for 2 h. The solid was precipitated, filtered, and the crude product was beated with anhydrous ethyl acetate (5 mL) to give a pale yellow solid, which was dried in vacuo to give the title product of 6,6-dimethyl-8-isopropyl-2-(5-(1-piperazinyl)-pyridin-2-amino)-6H-pyrimido[5,4-b][1,4]oxazin-7(8H)-one hydrochloride (I-1, 0.2 g, yield 46.0%), MS(m/z): 398 [M+H]$^+$. $^1$H NMR (DMSO-$d_6$): δ: 11.83 (br, 1H), 9.74 (br, 2H), 8.33 (s, 1H), 8.25-8.23 (d, J=8.0 Hz, 1H), 8.01 (s, 1H), 7.77-7.75 (d, J=8.0 Hz, 1H), 5.32-5.25 (m, 1H), 3.71-3.52 (m, 8H), 1.59 (s, 12H).

Embodiment 2
Compound (I-2)

6,6-Dimethyl-8-cyclopentyl-2-(5-(1-piperazinyl)-pyridin-2-amino)-6H-pyrimido[5,4-b][1,4]oxazin-7(8H)-one Compound I-2 was synthesized according to the method in Embodiment 1, and the starting materials were 2-chloro-6,6-dimethyl-8-cyclopentyl-6H-pyrimido[5,4-b][1,4]oxazin-7(8H)-one (its synthesis was similar to that in Embodiment 1, the starting materials were 2,4-dichloro-5-methoxypyrimidine and cyclopentylamine) and tert-butyl 4-(6-aminopyridin-3-yl)piperazine-1-carboxylate. The title product of 6,6-dimethyl-8-cyclopentyl-2-(5-(1-piperazinyl)-pyridin-2-amino)-6H-pyrimido[5,4-b][1,4]oxazin-7(8H)-one hydrochloride (I-2) was obtained as a pale yellow solid. MS(m/z): 424 [M+H]$^+$. $^1$H NMR (DMSO-$d_6$): δ: 11.88 (br, 1H), 9.77 (br, 2H), 8.26(s, 1H), 8.24-8.22 (d, J=8.0 Hz, 1H), 7.93(s, 1H), 7.70-7.68 (d, J=8.0 Hz, 1H), 5.37-5.23 (m, 1H), 4.61 (m, 4H), 3.45 (m, 4H), 2.05-1.55 (m, 8H), 1.48 (s, 6H).

Embodiment 3
Compound (I-3)

6,6-Dimethyl-8-cyclopentyl-2-(5-(4-ethyl-1-piperazinyl)methyl-pyridin-2-amino)-6H-pyrimido[5,4-b][1,4]oxazin-7(8H)-one The synthesis of Compound I-3 was synthesized according to the method in Embodiment 1, and the starting materials were 2-chloro-6,6-dimethyl-8-cyclopentyl-6H-pyrimidine[5,4-b][1,4]oxazin-7(8H)-one and 5-[(4-ethylpiperazin-1-yl)methyl]pyridin-2-amine. The title product of 6,6-dimethyl-8-cyclopentyl-2-(5-(4-ethyl-1-piperazinyl)methyl-pyridin-2-amino)-6H-pyrimido[5,4-b][1,4]oxazin-7(8H)-one hydrochloride (I-3) was obtained as a white solid. MS(m/z): 466 [M+H]$^+$. $^1$H NMR (DMSO-$d_6$): δ: 12.04(br, 1H), 11.83(br, 1H), 8.53(s, 1H), 8.36-8.34 (d, J=8.0 Hz, 1H), 8.19(s, 1H), 7.72-7.70 (d, J=8.0 Hz, 1H), 5.29-5.21 (m, 1H), 4.41 (m, 4H), 3.59-3.51 (m, 6H), 3.08 (m, 2H), 1.99-1.47 (m, 8H), 1.39 (s, 6H), 1.19-1.15 (t, J=8.0 Hz, 3H).

Embodiment 4
Compound (I-4)

8'-cyclopentyl-2'-(5-(1-piperazinyl)-pyridin-2-amino)spiro[cycloprop-1,6'-pyrimido[5,4-b][1,4]oxazin]-7'(8'H)-one Compound I-4 was synthesized according to the method in Embodiment 1, and the starting materials were 2'-chloro-8'-cyclopentyl-spiro[cycloprop-1,6'-pyrimido[5,4-b][1,4]oxazin]-7'(8'H)-one (its synthesis was similar to that in Embodiment 1, the starting materials were 2,4-dichloro-5-methoxypyrimidine and methyl 1-bromocyclopropanecarboxylate) and tert-butyl 1-(2-pyridyl) 4-(6-aminopyridin-3-yl)piperazine-1-carboxylate. The title product of 8'-cyclopentyl-2'-(5-(1-piperazinyl)-pyridin-2-amino)spiro[cycloprop-1,6'-pyrimido[5,4-b][1,4]oxazin]-7'(8'H)-one hydrochloride (I-4) was obtained as a pale yellow solid.

MS(m/z): 422 [M+H]+. 1H NMR (DMSO-d$_6$): δ: 11.89(br, 1H), 9.80(br, 2H), 8.25(s, 1H), 8.23-8.21 (d, J=8.0 Hz, 1H), 7.92(s, 1H), 7.70-7.68 (d, J=8.0 Hz, 1H), 5.36-5.23 (m, 1H), 4.60 (m, 4H), 3.47 (m, 4H), 2.03-1.55 (m, 8H), 1.01-0.57 (m, 4H).

Embodiment 5
Compound (I-5)

8'-cyclopentyl-2'-(5-(1-piperazinyl)-pyridin-2-amino)spiro[cyclobut-1,6'-pyrimido[5,4-b][1,4]oxazin]-7'(8'H)-one Compound I-5 was synthesized according to the method in Embodiment 1, and the starting materials were 2'-chloro-8'-cyclopentyl-spiro[cyclobut-1,6'-pyrimido[5,4-b][1,4]oxazin]-7'(8'H)-one (its synthesis was similar to that in Embodiment 1, the starting materials were 2,4-dichloro-5-methoxypyrimidine and methyl 1-bromocyclobutanecarboxylate) and tert-butyl 1-(2-pyridyl) 4-(6-aminopyridin-3-yl)piperazine-1-carboxylate. The title product of 8'-cyclopentyl-2'-(5-(1-piperazinyl)-pyridin-2-amino)spiro[cyclobut-1,6'-pyrimido[5,4-b][1,4]oxazin]-7'(8'H)-one hydrochloride (I-5) was obtained as a pale yellow solid. MS(m/z): 436 [M+H]+. 1H NMR (DMSO-d$_6$): δ: 11.87(br, 1H), 9.79(br, 2H), 8.26(s, 1H), 8.24-8.22 (d, J=8.0 Hz, 1H), 7.91(s, 1H), 7.70-7.68 (d, J=8.0 Hz, 1H), 5.35-5.23 (m, 1H), 4.55 (m, 4H), 3.45 (m, 4H), 2.71-2.59 (m, 4H), 2.03-1.98 (m, 2H), 1.75-1.57 (m, 8H).

Embodiment 6
Compound (I-6)

8'-cyclopentyl-2'-(5-(1-piperazinyl)-pyridin-2-amino)spiro[cyclopenta-1,6'-pyrimido[5,4-b][1,4]oxazin]-7'(8'H)-one Compound I-6 was synthesized according to the method in Embodiment 1, and the starting material was 2'-chloro-8'-cyclopentyl-spiro[cyclopenta-1,6'-pyrimido[5,4-b][1,4]oxazin]-7'(8'H)-one (its synthesis was similar to that in Embodiment 1, starting materials were 2,4-dichloro-5-methoxypyrimidine and methyl 1-bromocyclopentanecarboxylate) and tert-butyl 1-(2-pyridyl) 4-(6-aminopyridin-3-yl)piperazine-1-carboxylate. The title product of 8'-cyclopentyl-2'-(5-(1-piperazinyl)-pyridin-2-amino)spiro[cyclopenta-1,6'-pyrimido[5,4-b][1,4]oxazin]-7'(8'H)-one hydrochloride (I-6) was obtained as a pale yellow solid. MS(m/z): 450 [M+H]+. 1H NMR (DMSO-d$_6$): δ: 11.88 (br, 1H), 9.81 (br, 2H), 8.27 (s, 1H), 8.24-8.22 (d, J=8.0 Hz, 1H), 7.90 (s, 1H), 7.70-7.68 (d, J=8.0 Hz, 1H), 5.34-5.23 (m, 1H), 4.59 (m, 4H), 3.47 (m, 4H), 2.25-2.10 (m, 4H), 2.03-1.58 (m, 12H).

Embodiment 7
Compound (I-7)

8'-cyclopentyl-2'-(5-(1-piperazinyl)-pyridin-2-amino)spiro[cyclohex-1,6'-pyrimido[5,4-b][1,4]oxazin]-7'(8'H)-one Compound I-7 was synthesized according to the method in Embodiment 1, and the starting material was 2'-chloro-8'-cyclopentyl-spiro[cyclohex-1,6'-pyrimido[5,4-b][1,4]oxazin]-7'(8'H)-one (its synthesis was similar to that in Embodiment 1, and starting materials were 2,4-dichloro-5-methoxypyrimidine and methyl 1-bromocyclohexanecarboxylate) and tert-butyl 1-(2-pyridyl) 4-(6-aminopyridin-3-yl)piperazine-1-carboxylate. The title product of 8'-cyclopentyl-2'-(5-(1-piperazinyl)-pyridin-2-amino)spiro[cyclohex-1,6'-pyrimido[5,4-b][1,4]oxazin]-7'(8'H)-one hydrochloride (I-7) was obtained as a pale yellow solid. MS(m/z): 464 [M+H]+. 1H NMR (DMSO-d$_6$): δ: 11.87(br, 1H), 9.79(br, 2H), 8.27(s, 1H), 8.25-8.23 (d, J=8.0 Hz, 1H), 7.89(s, 1H), 7.70-7.68 (d, J=8.0 Hz, 1H), 5.35-5.23 (m, 1H), 4.65 (m, 4H), 3.57 (m, 4H), 2.23-1.95 (m, 4H), 1.93-1.54 (m, 14H).

Embodiment 8
Compound (I-8)

8'-cyclopentyl-2'-(5-(1-piperazinyl)-pyridin-2-amino)spiro[cyclohepta-1,6'-pyrimido[5,4-b][1,4]oxazin]-7'(8'H)-one Compound I-8 was synthesized according to the method in Embodiment 1, and the starting material was 2'-chloro-8'-cyclopentyl-spiro[cyclohept-1,6'-pyrimido[5,4-b][1,4]oxazin]-7'(8'H)-one (its synthesis was similar to that in Embodiment 1, and the starting materials were 2,4-dichloro-5-methoxypyrimidine and methyl 1-bromocycloheptanecarboxylate) and tert-butyl 1-(2-pyridyl) 4-(6-aminopyridin-3-yl)piperazine-1-carboxylate. The title product of 8'-cyclopentyl-2'-(5-(1-piperazinyl)-pyridin-2-amino)spiro[cyclohept-1,6'-pyrimido[5,4-b][1,4]oxazin]-7'(8'H)-one hydrochloride (I-8) was obtained as a pale yellow solid. MS(m/z): 478 [M+H]+. 1H NMR (DMSO-d$_6$): δ: 11.88 (br, 1H), 9.78 (br, 2H), 8.28 (s, 1H), 8.25-8.23 (d, J=8.0 Hz, 1H), 7.91 (s, 1H), 7.71-7.69 (d, J=8.0 Hz, 1H), 5.37-5.23 (m, 1H), 4.63 (m, 4H), 3.58 (m, 4H), 2.21-1.95 (m, 4H), 1.91-1.46 (m, 16H).

Embodiment 9
Compound (I-9)

6-acetyl-8-cyclopentyl-2-(5-(1-piperazinyl)-pyridin-2-amino)-6H-pyrimido[5,4-b][1,4]oxazin-7(8H)-one Compound I-9 was synthesized according to the method in Embodiment 1, and the starting material was 2-chloro-6-acetyl-8-cyclopentyl-6H-pyrimido[5,4-b][1,4]oxazin-7(8H)-one (its synthesis was similar to that in Embodiment 1, and the starting materials were 2,4-dichloro-5-methoxypyrimidine and methyl 2-bromo-2-carbonylacetate) and tert-butyl 1-(2-pyridyl) 4-(6-aminopyridin-3-yl)piperazine-1-carboxylate. The title product of 6-acetyl-8-cyclopentyl-2-(5-(1-piperazinyl)-pyridin-2-amino)-6H-pyrimido[5,4-b][1,4]oxazin-7(8H)-one hydrochloride (I-9) was obtained as a pale yellow solid. MS(m/z): 438 [M+H]+. 1H NMR (DMSO-d$_6$): δ: 11.87(br, 1H), 9.81 (br, 2H), 8.27(s, 1H), 8.25-8.23 (d, J=8.0 Hz, 1H), 7.90(s, 1H), 7.71-7.69 (d, J=8.0 Hz, 1H), 5.57 (s, 1H), 5.35-5.26 (m, 1H), 4.61 (m, 4H), 3.59 (m, 4H), 3.37 (s, 3H), 2.09-1.57 (m, 8H).

Embodiment 10
Compound (I-10)

6-cyano-8-cyclopentyl-2-(5-(1-piperazinyl)-pyridin-2-amino)-6H-pyrimido[5,4-b][1,4]oxazin-7(8H)-one Compound I-10 was synthesized according to the method in Embodiment 1, and the starting material was 2-chloro-6-cyano-8-cyclopentyl-6H-pyrimido[5,4-b][1,4]oxazin-7(8H)-one (its synthesis was similar to that in Embodiment 1, and the starting materials were 2,4-dichloro-5-methoxypyrimidine and methyl 2-bromo-2-cyanoacetate) and tert-butyl 1-(2-pyridyl) 4-(6-aminopyridin-3-yl)piperazine-1-carboxylate. The title product of 6-cyano-8-cyclopentyl-2-(5-(1-piperazinyl)-pyridin-2-amino)-6H-pyrimido[5,4-b][1,4]oxazin-7(8H)-one hydrochloride (I-10) was obtained as a pale yellow solid. MS(m/z): 421 [M+H]$^+$. $^1$H NMR (DMSO-d$_6$): δ: 11.89(br, 1H), 9.80(br, 2H), 8.28(s, 1H), 8.26-8.24 (d, J=8.0 Hz, 1H), 7.91(s, 1H), 7.71-7.69 (d, J=8.0 Hz, 1H), 5.58(s, 1H), 5.36-5.26 (m, 1H), 4.62 (m, 4H), 3.59 (m, 4H), 2.03-1.57 (m, 8H).

Embodiment 11
Compound (I-11)

6-trifluoromethyl-8-cyclopentyl-2-(5-(1-piperazinyl)-pyridin-2-amino)-6H-pyrimido[5,4-b][1,4]oxazin-7(8H)-one Compound I-11 was synthesized according to the method in Embodiment 1, and the starting material was 2-chloro-6-trifluoromethyl-8-cyclopentyl-6H-pyrimido[5,4-b][1,4]oxazin-7(8H)-one (its synthesis was similar to that in Embodiment 1, and the starting materials were 2,4-dichloro-5-methoxypyrimidine and methyl 2-bromo-2-trifluoromethylacetate) and tert-butyl 1-(2-pyridyl) 4-(6-aminopyridin-3-yl)piperazine-1-carboxylate. The title product of 6-trifluoromethyl-8-cyclopentyl-2-(5-(1-piperazinyl)-pyridin-2-amino)-6H-pyrimido[5,4-b][1,4]oxazin-7(8H)-one hydrochloride (I-11) was obtained as a pale yellow solid. MS(m/z): 464 [M+H]$^+$. $^1$H NMR (DMSO-d$_6$): δ: 11.87(br, 1H), 9.81(br, 2H), 8.27(s, 1H), 8.26-8.24 (d, J=8.0 Hz, 1H), 7.90(s, 1H), 7.70-7.68 (d, J=8.0 Hz, 1H), 5.57-5.54(m, 1H), 5.35-5.26 (m, 1H), 4.61 (m, 4H), 3.64 (m, 4H), 2.01-1.54 (m, 8H).

Embodiment 12
Compound (I-12)

6,6-difluoro-8-cyclopentyl-2-(5-(1-piperazinyl)-pyridin-2-amino)-6H-pyrimido[5,4-b][1,4]oxazin-7(8H)-one Compound I-12 was synthesized according to the method in Embodiment 1, and the starting material was 2-chloro-6,6-difluoro-8-cyclopentyl-6H-pyrimido[5,4-b][1,4]oxazin-7(8H)-one (its synthesis was similar to that in Embodiment 1, and the starting materials were 2,4-dichloro-5-methoxypyrimidine and methyl 2-bromo-2,2-difluoroacetate) and tert-butyl 1-(2-pyridyl) 4-(6-aminopyridin-3-yl)piperazine-1-carboxylate. The title product of 6,6-difluoro-8-cyclopentyl-2-(5-(1-piperazinyl)-pyridin-2-amino)-6H-pyrimido[5,4-b][1,4]oxazin-7(8H)-one hydrochloride (I-12) was obtained as a pale yellow solid. MS(m/z): 432 [M+H]$^+$. $^1$H NMR (DMSO-d$_6$): δ: 11.88 (br, 1H), 9.79 (br, 2H), 8.26 (s, 1H), 8.23-8.21 (d, J=8.0 Hz, 1H), 7.90 (s, 1H), 7.70-7.67 (d, J=8.0 Hz, 1H), 5.37-5.26 (m, 1H), 4.62 (m, 4H), 3.63 (m, 4H), 2.03-1.57 (m, 8H).

Embodiment 13
Compound (I-13)

6-cyclopropyl-8-cyclopentyl-2-(5-(1-piperazinyl)-pyridin-2-amino)-6H-pyrimido[5,4-b][1,4]oxazin-7(8H)-one Compound I-13 was synthesized according to the method in Embodiment 1, and the starting materials were 2-chloro-6-cyclopropyl-8-cyclopentyl-6H-pyrimido[5,4-b][1,4]oxazin-7(8H)-one (its synthesis was similar to that in Embodiment 1, and the starting materials were 2,4-dichloro-5-methoxypyrimidine and methyl 2-bromo-2-cyclopropylacetate) and 1-(2-pyridyl) and tert-butyl 4-(6-aminopyridin-3-yl)piperazine-1-carboxylate. The title product of 6-cyclopropyl-8-cyclopentyl-2-(5-(1-piperazinyl)-pyridin-2-amino)-6H-pyrimido[5,4-b][1,4]oxazin-7 (8H)-one hydrochloride (I-13) was obtained as a pale yellow solid. MS(m/z): 436 [M+H]$^+$. $^1$H NMR (DMSO-d$_6$): δ: 11.89(br, 1H), 9.81(br, 2H), 8.27(s, 1H), 8.24-8.22 (d, J=8.0 Hz, 1H), 7.89(s, 1H), 7.70-7.68 (d, J=8.0 Hz, 1H), 5.58-5.57 (d, J=4.0 Hz, 1H), 5.38-5.26 (m, 1H), 4.67 (m, 4H), 3.69 (m, 4H), 2.03-1.58 (m, 8H), 1.05-1.01 (m, 1H), 0.87-0.69 (m, 4H).

Embodiment 14
Compound (I-14)

6-cyclobutyl-8-cyclopentyl-2-(5-(4-ethyl-1-piperazinyl)methyl-pyridin-2-amino)-6H-pyrimido[5,4-b][1,4]oxazin-7(8H)-one Compound I-14 was synthesized according to the method in Embodiment 1, and the starting material was 2-chloro-6-cyclobutyl-8-cyclopentyl-6H-pyrimido[5,4-b][1,4]oxazin-7(8H)-one (its synthesis was similar to that in Embodiment 1, and the starting materials were 2,4-dichloro-5-methoxypyrimidine and methyl 2-bromo-2-butylpropyl acetate) and 5-[(4-ethylpiperazin-1-yl)methyl]pyridin-2-amine. The title product of 6-cyclobutyl-8-cyclopentyl-2-(5-(4-ethyl-1-piperazinyl)methyl-pyridin-2-amino)-6H-pyrimido[5,4-b][1,4]oxazin-7(8H)-one (I-14) was obtained as a white solid. MS(m/z): 492 [M+H]$^+$. $^1$H NMR (DMSO-d$_6$): δ: 11.81(br, 1H), 8.53 (s, 1H), 8.35-8.33 (d, J=8.0 Hz, 1H), 8.20(s, 1H), 7.71-7.69 (d, J=8.0 Hz, 1H), 5.58-5.57 (d, J=4.0 Hz, 1H), 5.27-5.21 (m, 1H), 4.87 (s, 2H), 4.45-4.23 (m, 11H), 2.47-2.21 (m, 14H), 1.19-1.15 (t, J=8.0 Hz, 3H).

Embodiment 15
Compound (I-15)

6-isopropyl-8-methyl-2-(5-(4-ethyl-1-piperazinyl)methyl-pyridin-2-amino)-6H-pyrimido[5,4-b][1,4]oxazin-7(8H)-one Compound I-15 was synthesized according to the method in Embodiment 1, and the starting material was 2-chloro-6-isopropyl-8-methyl-6H-pyrimido[5,4-b][1,4]oxazin-7(8H)-one (its synthesis was similar to that in Embodiment 1, and the starting materials were 2,4-dichloro-5-methoxypyrimidine, methylamine and methyl 2-bromoisovalerate) and 5-[(4-ethylpiperazin-1-yl)methyl]pyridin-2-amine. The title product of 6-isopropyl-8-methyl-2-(5-(4-ethyl-1-piperazinyl)methyl-pyridin-2-amino)-6H-pyrimido[5,4-b][1,4]oxazin-7(8H)-one (I-15) was obtained as a white solid. MS(m/z): 426 [M+H]$^+$. $^1$H NMR (DMSO-d$_6$): δ: 11.81 (br, 1H), 8.55(s, 1H), 8.35-8.33 (d, J=8.0 Hz, 1H), 8.18(s, 1H), 7.70-7.68 (d, J=8.0 Hz, 1H), 5.58-5.57 (d, J=4.0 Hz, 1H), 4.89(s, 2H), 4.59 (s, 3H), 4.41-4.23 (m, 11H), 1.19-1.15 (t, J=8.0 Hz, 3H), 1.05-1.04 (d, J=4.0 Hz, 6H).

Embodiment 16
Compound (I-16)

6-methyl-6,8-diethyl-2-(5-(4-methyl-1-piperazinyl)methyl-pyridin-2-amino)-6H-pyrimido[5,4-b][1,4]oxazin-7(8H)-one Compound I-16 was synthesized according to the method in Embodiment 1, and the starting material was 2-chloro-6-methyl-6,8-diethyl-6H-pyrimido[5,4-b][1,4]oxazin-7(8H)-one (its synthesis was similar to that in Embodiment 1, and the starting materials were 2,4-dichloro-5-methoxypyrimidine, ethylamine and methyl 2-bromo-2-methylbutylate) and 5-[(4-methylpiperazin-1-yl)methyl]pyridin-2-amine. The title product of 6-methyl-6,8-diethyl-2-(5-(4-methyl-1-piperazinyl)methyl-pyridin-2-amino)-6H-pyrimido[5,4-b]

[1,4]oxazin-7(8H)-one (I-16) was obtained as a white solid. MS(m/z): 426 [M+H]$^+$. $^1$H NMR (DMSO-d$_6$): δ: 11.82(br, 1H), 8.56(s, 1H), 8.35-8.33 (d, J=8.0 Hz, 1H), 8.19(s, 1H), 7.70-7.68 (d, J=8.0 Hz, 1H), 4.89 (s, 2H), 4.67-4.63 (q, J=4.0 Hz, 2H), 4.59 (s, 3H), 4.40-4.22 (m, 8H), 3.25-3.21 (q, J=4.0 Hz, 2H), 2.35 (s, 3H), 2.01-1.99 (t, J=4.0 Hz, 3H), 1.58-1.56 (t, J=4.0 Hz, 3H).

Embodiment 17

Compound (I-17)

6-cyclopentyl-8-sec-butyl-2-(5-(1-piperazinyl)methyl-pyridin-2-amino)-6H-pyrimido[5,4-b][1,4]thiazin-7(8H)-one Compound I-17 was synthesized according to the method in Embodiment 1, and the starting material was 2-chloro-6-cyclopentyl-8-sec-butyl-6H-pyrimidine[5,4-b][1,4]thiazin-7(8H)-one (its synthesis was similar to that in Embodiment 1, and the starting materials were 2,4-dichloro-5-methylthiopyrimidine, sec-butylamine and methyl 2-bromo-2-cyclopentyl acetate) and 5-[(piperazin-1-yl)methyl]pyridin-2-amine. The title product of 6-cyclopentyl-8-sec-butyl-2-(5-(1-piperazinyl)methyl-pyridin-2-amino)-6H-pyrimido[5,4-b][1,4]thiazin-7(8H)-one hydrochloride (I-17) was obtained as a white solid. MS(m/z): 482 [M+H]$^+$. $^1$H NMR (DMSO-d$_6$): δ: 11.89 (br, 1H), 9.81 (br, 2H), 8.55(s, 1H), 8.35-8.33 (d, J=8.0 Hz, 1H), 8.21(s, 1H), 7.70-7.68 (d, J=8.0 Hz, 1H), 4.88-4.65(m, 4H), 4.42-4.25 (m, 8H), 2.21-1.95(m, 14H), 0.98-0.96 (t, J=4.0 Hz, 3H).

Embodiment 18

Compound (I-18)

6-cyclohexyl-8-tert-amyl-2-(5-(4-cyclopropyl-1-piperazinyl)methyl-pyridin-2-amino)-6H-pyrimido[5,4-b][1,4]oxazin-7(8H)-one Compound I-18 was synthesized according to the method in Embodiment 1, and the starting material was 2-chloro-6-cyclohexyl-8-tert-amyl-6H-pyrimido[5,4-b][1,4]oxazin-7(8H)-one (its synthesis was similar to that in Embodiment 1, and the starting materials were 2,4-dichloro-5-methoxypyrimidine, tert-amylamine and methyl 2-bromo-2-cyclohexylacetate) and 5-[(4-cyclopropylpiperazin-1-yl)methyl]pyridin-2-amine. The title product of 6-cyclohexyl-8-tert-amyl-2-(5-(4-cyclopropyl-1-piperazinyl)methyl-pyridin-2-amino)-6H-pyrimido[5,4-b][1,4]oxazin-7(8H)-one (I-18) was obtained as a white solid. MS(m/z): 534 [M+H]$^+$. $^1$H NMR (DMSO-d$_6$): δ: 11.81 (br, 1H), 8.57(s, 1H), 8.34-8.32 (d, J=8.0 Hz, 1H), 8.19(s, 1H), 7.70-7.68 (d, J=8.0 Hz, 1H), 5.58-5.57 (d, J=4.0 Hz, 1H), 4.88(s, 2H), 4.42-4.21 (m, 9H), 2.21-2.01 (m, 19H), 1.19-1.15 (t, J=8.0 Hz, 1H), 0.75-0.69 (m, 4H).

Embodiment 19

Compound (I-19)

6-cycloheptyl-8-(3-methyl-2-butyl)-2-(5-(4-n-propyl-1-piperazinyl)methyl-pyridine-2-amino)-6H-pyrimido[5,4-b][1,4]thiazin-7(8H)-one Compound I-19 was synthesized according to the method in Embodiment 1, and the starting material was 2-chloro-6-cycloheptyl-8-(3-methyl-2-butyl)-6H-pyrimido[5,4-b][1,4]thiazin-7(8H)-one (its synthesis was similar to that in Embodiment 1, and the starting materials were 2,4-dichloro-5-methylthiopyrimidine, 3-methyl-2-butylamine and methyl 2-bromo-2-cycloheptylacetate) and 5-[(4-propylpiperazin-1-yl)methyl]pyridin-2-amine. The title product of 6-cycloheptyl-8-(3-methyl-2-butyl)-2-(5-(4-n-propyl-1-piperazinyl)methyl-pyridin-2-amino)-6H-pyrimido[5,4-b][1,4]thiazin-7(8H)-one (I-19) was obtained as a white solid. MS(m/z): 567 [M+H]$^+$. $^1$H NMR (DMSO-d$_6$): δ: 11.82 (br, 1H), 8.55 (s, 1H), 8.34-8.32 (d, J=8.0 Hz, 1H), 8.21 (s, 1H), 7.70-7.68 (d, J=8.0 Hz, 1H), 5.58-5.57 (d, J=4.0 Hz, 1H), 4.87-4.65 (m, 4H), 4.43-4.21 (m, 11H), 2.19-2.01 (m, 17H), 1.21-1.18 (m, 9H).

Embodiment 20

Compound (I-20)

6,6-dimethyl-8-cyclopentyl-2-(5-(4-cyclobutyl-1-piperazinyl)-pyridin-2-amino)-6H-pyrimido[5,4-b][1,4]oxazin-7(8H)-one Compound I-20 was synthesized according to the method in Embodiment 1, and the starting materials were 2-chloro-6,6-dimethyl-8-cyclopentyl-6H-pyrimido[5,4-b][1,4]oxazin-7(8H)-one and 1-cyclobutyl-4-(6-aminopyridin-3-yl)piperazine. The title product of 6,6-dimethyl-8-cyclopentyl-2-(5-(4-cyclobutyl-1-piperazinyl)-pyridin-2-amino)-6H-pyrimido[5,4-b][1,4]oxazin-7(8H)-one (I-20) was obtained as a pale yellow solid. MS(m/z): 478 [M+H]$^+$. $^1$H NMR (DMSO-d$_6$): δ: 11.83(br, 1H), 8.26 (s, 1H), 8.22-8.20 (d, J=8.0 Hz, 1H), 7.91(s, 1H), 7.70-7.68 (d, J=8.0 Hz, 1H), 5.37-5.23 (m, 1H), 4.61-4.56 (m, 5H), 3.45-3.40 (m, 4H), 2.05-1.47 (m, 20H).

Embodiment 21

Compound (I-21)

6,6-dimethyl-8-cyclopentyl-2-(5-(4-cyclopentyl-1-piperazinyl)-pyridin-2-amino)-6H-pyrimido[5,4-b][1,4]oxazin-7(8H)-one Compound I-21 was synthesized according to the method in Embodiment 1, and the starting materials were 2-chloro-6,6-dimethyl-8-cyclopentyl-6H-pyrimido[5,4-b][1,4]oxazin-7(8H)-one and 1-cyclopentyl-4-(6-aminopyridin-3-yl)piperazine. The title product of 6,6-dimethyl-8-cyclopentyl-2-(5-(4-cyclopentyl-1-piperazinyl)-pyridin-2-amino)-6H-pyrimido[5,4-b][1,4]oxazin-7(8H)-one (I-21) was obtained as a pale yellow solid. MS(m/z): 492 [M+H]$^+$. $^1$H NMR (DMSO-d$_6$): δ: 11.81 (br, 1H), 8.25 (s, 1H), 8.23-8.21 (d, J=8.0 Hz, 1H), 7.92 (s, 1H), 7.70-7.68 (d, J=8.0 Hz, 1H), 5.36-5.23 (m, 1H), 4.60 (m, 4H), 3.45-3.39 (m, 5H), 2.03-1.43 (m, 22H).

Embodiment 22

Compound (I-22)

6,6-dimethyl-8-cyclopentyl-2-(5-(4-cyclohexyl-1-piperazinyl)-pyridin-2-amino)-6H-pyrimido[5,4-b][1,4]oxazin-7(8H)-one Compound I-22 was synthesized according to the method in Embodiment 1, and the starting materials were 2-chloro-6,6-dimethyl-8-cyclopentyl-6H-pyrimido[5,4-b][1,4]oxazin-7(8H)-one and 1-cyclohexyl-4-(6-aminopyridin-3-yl)piperazine. The title product of 6,6-dimethyl-8-cyclopentyl-2-(5-(4-cyclohexyl-1-piperazinyl)-pyridin-2-amino)-6H-pyrimido[5,4-b][1,4]oxazin-7(8H)-one (I-22) was obtained as a pale yellow solid. MS(m/z): 506 [M+H]$^+$. $^1$H NMR (DMSO-d$_6$): δ: 11.83(br, 1H), 8.26(s, 1H), 8.23-8.21 (d, J=8.0 Hz, 1H), 7.93(s, 1H), 7.70-7.68 (d, J=8.0 Hz, 1H), 5.35-5.25 (m, 1H), 4.61 (m, 4H), 3.47-3.39 (m, 5H), 2.05-1.43 (m, 24H).

Embodiment 23
Compound (I-23)

6,6-dimethyl-8-cyclopentyl-2-(5-(4-cycloheptyl-1-piperazinyl)-pyridin-2-amino)-6H-pyrimido[5,4-b][1,4]thiazin-7(8H)-one Compound I-23 was synthesized according to the method in Embodiment 1, and the starting materials were 2-chloro-6,6-dimethyl-8-cyclopentyl-6H-pyrimido[5,4-b][1,4]thiazin-7(8H)-one and 1-cycloheptyl-4-(6-aminopyridin-3-yl)piperazine. The title product of 6,6-dimethyl-8-cyclopentyl-2-(5-(4-cycloheptyl-1-piperazinyl)-pyridin-2-amino)-6H-pyrimido[5,4-b][1,4]thiazin-7(8H)-one (I-23) was obtained as a pale yellow solid. MS(m/z): 536 [M+H]$^+$. $^1$H NMR (DMSO-d$_6$): δ: 11.81 (br, 1H), 8.27 (s, 1H), 8.22-8.20 (d, J=8.0 Hz, 1H), 7.91 (s, 1H), 7.71-7.69 (d, J=8.0 Hz, 1H), 5.35-5.25 (m, 1H), 4.61 (m, 4H), 3.46-3.37 (m, 5H), 2.07-1.42 (m, 26H).

Embodiment 24
Compound (I-24)

6,6-dimethyl-8-cyclopentyl-2-(5-(4-isopropyl-1-piperazinyl)-pyridin-2-amino)-6H-pyrimido[5,4-b][1,4]thiazin-7(8H)-one Compound I-24 was synthesized according to the method in Embodiment 1, and the starting materials were 2-chloro-6,6-dimethyl-8-cyclopentyl-6H-pyrimido[5,4-b][1,4]thiazin-7(8H)-one and 1-isopropyl-4-(6-aminopyridin-3-yl)piperazine. The title product of 6,6-dimethyl-8-cyclopentyl-2-(5-(4-isopropyl-1-piperazinyl)-pyridin-2-amino)-6H-pyrimido[5,4-b][1,4]thiazin-7(8H)-one (I-24) was obtained as a pale yellow solid. MS(m/z): 482 [M+H]$^+$. $^1$H NMR (DMSO-d$_6$): δ: 11.82 (br, 1H), 8.26 (s, 1H), 8.23-8.21 (d, J=8.0 Hz, 1H), 7.91 (s, 1H), 7.71-7.69 (d, J=8.0 Hz, 1H), 5.38-5.27 (m, 1H), 4.63 (m, 4H), 3.47-3.37 (m, 5H), 2.01-1.45 (m, 14H), 1.58-1.57 (d, J=4.0 Hz, 6H).

Embodiment 25
Compound (I-25)

8'-cyclopentyl-2'-(5-(4-ethyl-1-piperazinyl)-pyridin-2-amino)spiro[cycloprop-1,6'-pyrimido[5,4-b][1,4]oxazin]-7'(8'H)-one Compound I-25 was synthesized according to the method in Embodiment 1, and the starting materials were 2'-chloro-8'-cyclopentyl-spiro[cycloprop-1,6'-pyrimido[5,4-b][1,4]oxazin]-7'(8'H)-one and 1-(2-pyridyl) and 5-[(4-ethylpiperazin-1-yl)methyl]pyridin-2-amine. The title product of 8'-cyclopentyl-2'-(5-(4-ethyl-1-piperazinyl)-pyridin-2-amino)spiro[cycloprop-1,6'-pyrimido[5,4-b][1,4]oxazin]-7'(8'H)-one (I-25) was obtained as a pale yellow solid. MS(m/z): 464 [M+H]$^+$. $^1$H NMR (DMSO-d$_6$): δ: 11.83 (br, 1H), 8.53 (s, 1H), 8.36-8.34 (d, J=8.0 Hz, 1H), 8.21 (s, 1H), 7.71-7.69 (d, J=8.0 Hz, 1H), 5.01-4.95 (m, 3H), 4.25-3.56 (m, 10H), 2.05-1.57 (m, 8H), 1.21-0.97 (m, 7H).

Embodiment 26
Compound (I-26)

6-acetyl-8-cyclopentyl-2-(5-(4-ethyl-1-piperazinyl)methyl-pyridin-2-amino)-6H-pyrimido[5,4-b][1,4]oxazin-7(8H)-one Compound I-26 was synthesized according to the method in Embodiment 1, and the starting materials were 2-chloro-6-acetyl-8-cyclopentyl-6H-pyrimido[5,4-b][1,4]oxazin-7(8H)-one and 1-(2-pyridyl) and 5-[(4-ethylpiperazin-1-yl)methyl]pyridin-2-amine. The title product of 6-acetyl-8-cyclopentyl-2-(5-(4-ethyl-1-piperazinyl)methyl-pyridin-2-amino)-6H-pyrimido[5,4-b][1,4]oxazin-7(8H)-one (I-26) was obtained as a pale yellow solid. MS(m/z): 480 [M+H]$^+$. $^1$H NMR (DMSO-d$_6$): δ: 11.81 (br, 1H), 8.52 (s, 1H), 8.36-8.34 (d, J=8.0 Hz, 1H), 8.20 (s, 1H), 7.71-7.69 (d, J=8.0 Hz, 1H), 6.15 (s, 1H), 5.01-4.85 (m, 3H), 4.23-3.58 (m, 10H), 3.39 (s, 3H), 2.01-1.57 (m, 8H), 1.23-1.21 (t, J=4.0 Hz, 3H).

Embodiment 27
Compound (I-27)

6-cyano-8-cyclopentyl-2-(5-(4-ethyl-1-piperazinyl)methyl-pyridin-2-amino)-6H-pyrimido[5,4-b][1,4]oxazin-7(8H)-one Compound I-27 was synthesized according to the method in Example 1, and the starting materials were 2-chloro-6-cyano-8-cyclopentyl-6H-pyrimido[5,4-b][1,4]oxazin-7(8H)-one and 1-(2-pyridyl) and 5-[(4-ethylpiperazin-1-yl)methyl]pyridin-2-amine. The title product of 6-cyano-8-cyclopentyl-2-(5-(4-ethyl-1-piperazinyl)methyl-pyridin-2-amino)-6H-pyrimido[5,4-b][1,4]oxazin-7(8H)-one (I-27) was obtained as a pale yellow solid. MS(m/z): 463 [M+H]$^+$. $^1$H NMR (DMSO-d$_6$): δ: 11.80 (br, 1H), 8.51 (s, 1H), 8.37-8.35 (d, J=8.0 Hz, 1H), 8.21 (s, 1H), 7.71-7.69 (d, J=8.0 Hz, 1H), 6.17 (s, 1H), 5.00-4.87 (m, 3H), 4.21-3.58 (m, 10H), 2.01-1.58 (m, 8H), 1.24-1.22 (t, J=4.0 Hz, 3H).

Embodiment 28
Compound (I-28)

8'-cyclopentyl-2'-(5-(4-ethyl-1-piperazinyl)-pyridin-2-amino)spiro[cyclobut-1,6'-pyrimido[5,4-b][1,4]oxazin]-7'(8'H)-one Compound I-28 was synthesized according to the method in Embodiment 1, and the starting materials were 2'-chloro-8'-cyclopentyl-spiro[cyclobut-1,6'-pyrimido[5,4-b][1,4]oxazin]-7'(8'H)-one and 1-(2-pyridyl) and 5-[(4-ethylpiperazin-1-yl)methyl]pyridin-2-amine. The title product of 8'-cyclopentyl-2'-(5-(4-ethyl-1-piperazinyl)-pyridin-2-amino)spiro[cyclobut-1,6'-pyrimido[5,4-b][1,4]oxazin]-7'(8'H)-one (I-28) was obtained as a pale yellow solid. MS(m/z): 478 [M+H]$^+$. $^1$H NMR (DMSO-d$_6$): δ: 11.82 (br, 1H), 8.52 (s, 1H), 8.37-8.35 (d, J=8.0 Hz, 1H), 8.23 (s, 1H), 7.71-7.69 (d, J=8.0 Hz, 1H), 4.98-4.94 (m, 3H), 4.23-3.56 (m, 14H), 2.03-1.55 (m, 10H), 1.23-1.21 (t, J=4.0 Hz, 3H).

Embodiment 29
Compound (I-29)

6,6-dimethyl-8-(2-thienyl)-2-(5-(1-piperazinyl)-pyridin-2-amino)-6H-pyrimido[5,4-b][1,4]oxazin-7(8H)-one Compound I-29 was synthesized according to the method in Embodiment 1, and the starting material was 2-chloro-6,6-dimethyl-8-(2-thienyl)-6H-pyrimido[5,4-b][1,4]oxazin-7(8H)-one (its synthesis was similar to that in Embodiment 1, and the starting materials were 2,4-dichloro-5-methoxypyrimidine and 2-aminothiophene) and tert-butyl 4-(6-aminopyridin-3-yl)piperazine-1-carboxylate. The title product of 6,6-dimethyl-8-(2-thienyl)-2-(5-(1-piperazinyl)-pyridin-2-yl)-6H-pyrimido[5,4-b][1,4]oxazin-7(8H)-one hydrochloride (I-29) was obtained as a pale yellow solid. MS(m/z): 438 [M+H]$^+$. $^1$H NMR (DMSO-d$_6$): δ: 11.89 (br, 1H), 9.78

(br, 2H), 8.26 (s, 1H), 8.24-8.22 (d, J=8.0 Hz, 1H), 7.91-7.78 (m, 4H), 6.58-6.52 (m, 1H), 4.61 (m, 4H), 3.47 (m, 4H), 1.48 (s, 6H).

Embodiment 30
Compound (I-30)

6,6-dimethyl-8-(2-pyridyl)-2-(5-(4-ethyl-1-piperazinyl)methyl-pyridine-2-amino)-6H-pyrimido[5,4-b][1,4]oxazin-7(8H)-one Compound I-30 was synthesized according to the method in Embodiment 1, and the starting materials were 2-chloro-6,6-dimethyl-8-(2-pyridyl)-6H-pyrimidio[5,4-b][1,4]oxazin-7(8H)-one and 5-[(4-ethylpiperazin-1-yl)methyl]pyridin-2-amine. The title product of 6,6-dimethyl-8-(2-pyridyl)-2-(5-(4-ethyl-1-piperazinyl)methyl-pyridin-2-amino)-6H-pyrimido[5,4-b][1,4]oxazin-7(8H)-one (I-30) was obtained as a white solid. MS(m/z): 475 [M+H]$^+$. $^1$H NMR (DMSO-d$_6$): δ: 11.83 (br, 1H), 8.67-8.64 (m, 1H), 8.61-8.58 (m, 1H), 8.51-8.47 (m, 2H), 8.36-8.34 (d, J=8.0 Hz, 1H), 8.21 (s, 1H), 8.05-8.01 (m, 1H), 7.72-7.70 (d, J=8.0 Hz, 1H), 4.87 (s, 2H), 4.23-3.56 (m, 10H), 1.58 (s, 6H), 1.19-1.17 (t, J=4.0 Hz, 3H).

Embodiment 31
Compound (I-31)

6,6-dimethyl-8-(2-pyrimidinyl)-2-(5-(4-ethyl-1-piperazinyl)methyl-pyridine-2-amino)-6H-pyrimido[5,4-b][1,4]oxazin-7(8H)-one Compound I-31 was synthesized according to the method in Embodiment 1, and the starting materials were 2-chloro-6,6-dimethyl-8-(2-pyrimidinyl)-6H-pyrimido[5,4-b][1,4]oxazin-7(8H)-one and 5-[(4-ethylpiperazin-1-yl)methyl]pyridin-2-amine. The title product of 6,6-dimethyl-8-(2-pyrimidinyl)-2-(5-(4-ethyl-1-piperazinyl)methyl-pyridin-2-amino)-6H-pyrimido[5,4-b][1,4]oxazin-7(8H)-one (I-31) was obtained as a white solid. MS(m/z): 476 [M+H]$^+$. $^1$H NMR (DMSO-d$_6$): δ: 11.81 (br, 1H), 8.92-8.89 (m, 2H), 8.53 (s, 1H), 8.37-8.34 (m, 2H), 8.20 (s, 1H), 7.72-7.70 (d, J=8.0 Hz, 1H), 4.87 (s, 2H), 4.21-3.64 (m, 10H), 1.57 (s, 6H), 1.19-1.17 (t, J=4.0 Hz, 3H).

Embodiment 32
Compound (I-32)

6,6-dimethyl-8-(2-furyl)-2-(5-(1-piperazinyl)-pyridin-2-yl)-6H-pyrimido[5,4-b][1,4]oxazin-7(8H)-one Compound I-32 was synthesized according to the method in Embodiment 1, and the starting materials were 2-chloro-6,6-dimethyl-8-(2-furyl)-6H-pyrimido[5,4-b][1,4]oxazin-7(8H)-one and tert-butyl 4-(6-aminopyridin-3-yl)piperazine-1-carboxylate. The title product of 6,6-dimethyl-8-(2-furyl)-2-(5-(1-piperazinyl)-pyridin-2-amino)-6H-pyrimido[5,4-b][1,4]oxazin-7(8H)-one hydrochloride (I-32) was obtained as a pale yellow solid. MS(m/z): 422 [M+H]$^+$. $^1$H NMR (DMSO-d$_6$): δ: 11.87 (br, 1H), 9.81 (br, 2H), 8.25 (s, 1H), 8.24-8.22 (d, J=8.0 Hz, 1H), 7.98-7.82 (m, 3H), 6.57-6.52 (m, 2H), 4.62 (m, 4H), 3.48 (m, 4H), 1.51 (s, 6H).

Embodiment 33
Compound (I-33)

N,N-dimethyl-6-carboxamide-8-cyclopentyl-2-(5-(1-piperazinyl)-pyridin-2-amino)-6H-pyrimido[5,4-b][1,4]oxazin-7(8H)-one Compound I-33 was synthesized according to the method in Embodiment 1, and the starting materials were 2-chloro-N,N-dimethyl-6-carboxamide-8-cyclopentyl-6H-pyrimido[5,4-b][1,4]oxazin-7(8H)-one and 1-(2-pyridyl) and tert-butyl 4-(6-aminopyridin-3-yl)piperazine-1-carboxylate. The title product of N,N-dimethyl-6-carboxamide-8-cyclopentyl-2-(5-(1-piperazinyl)-pyridin-2-amino)-6H-pyrimido[5,4-b][1,4]oxazin-7(8H)-one hydrochloride (I-33) was obtained as a pale yellow solid. MS(m/z): 467 [M+H]$^+$. $^1$H NMR (DMSO-d$_6$): δ: 11.88(br, 1H), 9.80(br, 2H), 8.27 (s, 1H), 8.23-8.21 (d, J=8.0 Hz, 1H), 7.91(s, 1H), 7.71-7.69 (d, J=8.0 Hz, 1H), 5.58(s, 1H), 5.33-5.26 (m, 1H), 5.01 (s, 6H), 4.62 (m, 4H), 3.61 (m, 4H), 2.05-1.57 (m, 8H).

Embodiment 34
Compound (I-34)

6-carboxamide-8-cyclopentyl-2-(5-(1-piperazinyl)-pyridin-2-amino)-6H-pyrimido[5,4-b][1,4]oxazin-7(8H)-one Compound I-34 was synthesized according to the method in Embodiment 1, and the starting materials were 2-chloro-6-carboxamide-8-cyclopentyl-6H-pyrimido[5,4-b][1,4]oxazin-7(8H)-one and 1-(2-pyridyl) and tert-butyl 4-(6-aminopyridin-3-yl)piperazine-1-carboxylate. The title product of 6-carboxamide-8-cyclopentyl-2-(5-(1-piperazinyl)-pyridin-2-amino)-6H-pyrimido[5,4-b][1,4]oxazin-7(8H)-one hydrochloride (I-34) was obtained as a pale yellow solid. MS(m/z): 439 [M+H]$^+$. $^1$H NMR (DMSO-d$_6$): δ: 11.86 (br, 1H), 9.83 (br, 2H), 9.57 (br, 2H), 8.26 (s, 1H), 8.22-8.20 (d, J=8.0 Hz, 1H), 7.91 (s, 1H), 7.71-7.69 (d, J=8.0 Hz, 1H), 5.59 (s, 1H), 5.34-5.26 (m, 1H), 4.63 (m, 4H), 3.63 (m, 4H), 2.01-1.62 (m, 8H).

Embodiment 35
Compound (I-35)

6,6-dimethyl-8-phenyl-2-(5-(1-piperazinyl)-pyridin-2-amino)-6H-pyrimido[5,4-b][1,4]oxazin-7(8H)-one Compound I-35 was synthesized according to the method in Embodiment 1, and the starting material was 2-chloro-6,6-dimethyl-8-phenyl-6H-pyrimido[5,4-b][1,4]oxazin-7(8H)-one (its synthesis was similar to that in Embodiment 1, and the starting materials were 2,4-dichloro-5-methoxypyrimidine and aniline) and tert-butyl 4-(6-aminopyridin-3-yl)piperazine-1-carboxylate. The title product of 6,6-dimethyl-8-phenyl-2-(5-(1-piperazinyl)-pyridin-2-amino)-6H-pyrimido[5,4-b][1,4]oxazin-7(8H)-one (I-35) was obtained as a pale yellow solid. MS(m/z): 432 [M+H]$^+$. $^1$H NMR (DMSO-d$_6$): δ: 11.86 (br, 1H), 9.82 (br, 2H), 8.56-8.52 (m, 4H), 8.26 (s, 1H), 8.24-8.22 (d, J=8.0 Hz, 1H), 7.99-7.92 (m, 3H), 4.61 (m, 4H), 3.49 (m, 4H), 1.52 (s, 6H).

Embodiment 36
Compound (I-36)

6,6-dimethyl-8-(4-chlorophenyl)-2-(5-(1-piperazinyl)-pyridin-2-amino)-6H-pyrimido[5,4-b][1,4]oxazin-7(8H)-one Compound I-36 was synthesized according to the method in Embodiment 1, and the starting material was 2-chloro-6,6-dimethyl-8-(4-chlorophenyl)-6H-pyrimido[5,4-b][1,4]oxazin-7(8H)-one (its synthesis was similar to that in Embodiment 1, and the starting materials were 2,4-dichloro-5-methoxypyrimidine and 4-chlorophenylamine) and tert-butyl 4-(6-aminopyridin-3-yl)piperazine-1-carboxylate. The title product of 6,6-dimethyl-8-(4-chlorophenyl)-2-(5-(1-piperazinyl)-pyridin-2-amino)-6H-pyrimido[5,4-b][1,4]oxazin-7(8H)-one (I-36) was obtained as a pale yellow solid.

MS(m/z): 466 [M+H]+. 1H NMR (DMSO-d6): δ: 11.87 (br, 1H), 9.85 (br, 2H), 8.56-8.54 (d, J=8.0 Hz, 2H), 8.45-8.43 (d, J=8.0 Hz, 2H), 8.26 (s, 1H), 8.23-8.21 (d, J=8.0 Hz, 1H), 7.90 (s, 1H), 7.71-7.69 (d, J=8.0 Hz, 1H), 4.63 (m, 4H), 3.51 (m, 4H), 1.54 (s, 6H).

Embodiment 37
Compound (I-37)

6,6-dimethyl-8-(3-pentyl)-2-(5-(1-piperazinyl)-pyridin-2-amino)-6H-pyrimido[5,4-b][1,4]oxazin-7(8H)-one Compound I-37 was synthesized according to the method in Embodiment 1, and the starting materials were 2-chloro-6,6-dimethyl-8-(3-pentyl)-6H-pyrimido[5,4-b][1,4]oxazin-7(8H)-one and tert-butyl 4-(6-aminopyridin-3-yl)piperazine-1-carboxylate. The title product of 6,6-dimethyl-8-(3-pentyl)-2-(5-(1-piperazinyl)-pyridin-2-amino)-6H-pyrimido[5,4-b][1,4]oxazin-7(8H)-one hydrochloride (I-37) was obtained as a pale yellow solid. MS(m/z): 426 [M+H]+. 1H NMR (DMSO-d6): δ: 11.87 (br, 1H), 9.78 (br, 2H), 8.27 (s, 1H), 8.24-8.22 (d, J=8.0 Hz, 1H), 7.91 (s, 1H), 7.70-7.68 (d, J=8.0 Hz, 1H), 5.35-5.22 (m, 1H), 4.61 (m, 4H), 3.48 (m, 4H), 1.58 (s, 6H), 1.45-1.42 (m, 4H), 0.92-0.88 (m, 6H).

Embodiment 38
Compound (I-38)

6,6-dimethyl-8-(3-pentyl)-2-(5-(4-ethyl-1-piperazinyl)methyl-pyridine-2-amino)-6H-pyrimido[5,4-b][1,4]oxazin-7(8H)-one Compound I-37 was synthesized according to the method in Embodiment 1, and the starting materials were 2-chloro-6,6-dimethyl-8-(3-pentyl)-6H-pyrimido[5,4-b][1,4]oxazin-7(8H)-one and tert-butyl 4-(6-aminopyridin-3-yl)piperazine-1-carboxylate 5-[(4-ethylpiperazin-1-yl)methyl]pyridyl-2-amine. The title product of 6,6-dimethyl-8-(3-pentyl)-2-(5-(4-ethyl-1-piperazinyl)methyl-pyridin-2-amino)-6H-pyrimido[5,4-b][1,4]oxazin-7(8H)-one (I-38) was obtained as a pale yellow solid. MS(m/z): 468 [M+H]+. 1H NMR (DMSO-d6): δ: 11.82(br, 1H), 8.51 (s, 1H), 8.36-8.34 (d, J=8.0 Hz, 1H), 8.18 (s, 1H), 7.72-7.70 (d, J=8.0 Hz, 1H), 5.21-5.08 (m, 3H), 4.61-4.02 (m, 10H), 1.59(s, 6H), 1.46-1.42 (m, 4H), 0.93-0.88 (m, 9H).

Embodiment 39
Biological Assays

Activity Assay: The CDK4 protein kinase activity was measured using the Caliper mobility shift assay (see J. Biomol. Screen, 2009, PP31). The test compound was dissolved in DMSO and diluted with a kinase buffer solution (20 mM HEPES-pH 7.5, 0.01% Triton X-100, 10 mM MgCl2, 2 mM DTT) and 5 μL of the compound at 5-fold final concentration of reaction dissolved in 10% DMSO was added in a 384-well plate. The compound-free control well was 5 μL of 10% DMSO, and the no-activity control well was 5 μL of kinase buffer. 10 μL of a 2.5-fold diluted CDK4 enzyme solution (GST-CDK4(1-303 end)) was added and incubated at room temperature for 10 min, and then 10 μL of the 2.5-fold diluted substrate solution Peptide FAM-P8 was added. The reaction was stopped by adding 25 μL of stop solution after incubation at 28° C. for 3 h, and the conversion rate data was read on a Caliper EZ Reader II (Caliper Life Sciences) and the conversion rate was converted to inhibition rate data according to above method. Among them, the inhibition rate %=(max−conversion)/(max−min)×100%.

Activity Assay: The CDK6 protein kinase activity was measured using the Caliper mobility shift assay (see J. Biomol. Screen, 2009, PP31). The test compound was dissolved in DMSO and diluted with a kinase buffer solution (20 mM HEPES-pH 7.5, 0.01% Triton X-100, 10 mM MgCl2, 2 mM DTT) and 5 μL of the compound at 5-fold final concentration of reaction dissolved in 10% DMSO was added in a 384-well plate. The compound-free control well was 5 μL of 10% DMSO, and the no-activity control well was 5 μL of kinase buffer. 10 μL of a 2.5-fold diluted CDK6 enzyme solution (GST-CDK6(1-326 end)) was added and incubated at room temperature for 10 min, and then 10 μL of the 2.5-fold diluted substrate solution Peptide FAM-P8 was added. The reaction was stopped by adding 25 μL of stop solution after incubation at 28° C. for 3 h, and the conversion rate data was read on a Caliper EZ Reader II (Caliper Life Sciences) and the conversion rate was converted to inhibition rate data according to above method. Among them, the inhibition rate %=(max−conversion)/(max−min)×100%.

Results of above experiments are summaried in Table 2.

TABLE 2

| Results of the assay | | | | | |
|---|---|---|---|---|---|
| Compound | CDK4 | CDK6 | Compound | CDK4 | CDK6 |
| Palbociclib | D | D | I-1 | D | D |
| I-2 | D | D | I-3 | D | D |
| I-4 | D | C | I-5 | D | C |
| I-6 | D | C | I-7 | D | D |
| I-8 | D | C | I-9 | D | C |
| I-10 | D | B | I-11 | D | C |
| I-12 | D | C | I-13 | D | D |
| I-14 | D | D | I-15 | D | C |
| I-16 | D | D | I-17 | D | A |
| I-18 | D | D | I-19 | D | C |
| I-20 | D | D | I-21 | D | C |
| I-22 | D | D | I-23 | D | D |
| I-24 | D | D | I-25 | D | D |
| I-26 | D | B | I-27 | D | D |
| I-28 | D | C | I-29 | D | D |
| I-30 | D | C | I-31 | D | D |
| I-32 | D | A | I-33 | D | D |
| I-34 | D | D | I-35 | C | C |
| I-36 | D | D | I-37 | D | C |
| I-38 | D | C | | | |

Note:
A represents IC50 > 500 nM,
B represents 500 nM ≥ IC50 > 100 nM,
C represents 100 nM ≥ IC50 > 20 nM,
D represents IC50 ≤ 20 nM.

What is claimed is:
1. A heterocyclic-substituted pyridinopyrimidinone derivative, wherein which has the following Formula I or a pharmaceutically acceptable salt thereof:

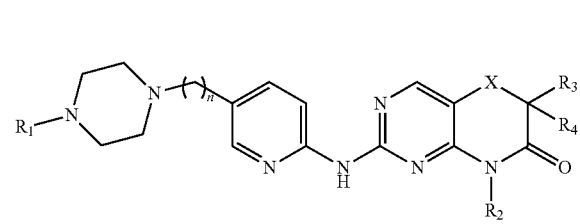

wherein,
R1 represents hydrogen, C1-C3 alkyl, or C3-C7 cycloalkyl;
R2 represents C1-C5 alkyl, or C3-C7 cycloalkyl;

$R_3$ and $R_4$ independently represents hydrogen, $C_1$-$C_3$ alkyl, $C_3$-$C_7$cycloalkyl, acetyl, halogen, trifluoromethyl, cyano or $CONR_5R_6$;

or $R_3$, $R_4$ together with the carbon atom to which they are attached form a $C_3$-$C_7$ aliphatic ring;

$R_5$ and $R_6$ independently represents hydrogen or methyl;

X represents O;

n is 0 or 1.

2. The heterocyclic-substituted pyridinopyrimidinone derivative according to claim 1, wherein the $C_1$-$C_3$ alkyl is methyl, ethyl, n-propyl, or iso-propyl, the $C_{1-5}$ alkyl is methyl, ethyl, n-propyl, iso-propyl, n-butyl, iso-butyl, sec-butyl, tert-butyl, 1-pentyl, 2-pentyl, 3-pentyl, 2-methyl-3-butyl, 1,1-dimethyl-1-propyl, or 2,2-dimethyl-1-propyl, and the $C_1$-$C_3$ alkoxy is methoxy, ethoxy, n-propoxy, or iso-propoxy.

3. The heterocyclic-substituted pyridinopyrimidinone derivative according to claim 1, wherein the $C_3$-$C_7$ cycloalkyl is cyclopropyl, cyclobutyl, cyclopentyl, cyclohexyl, or cycloheptyl, and the halogen is F, Cl, Br, or I.

4. The heterocyclic-substituted pyridinopyrimidinone derivative according to claim 1, wherein the derivative is a compound selected from the group consisting of:

| Compound | Structure |
|---|---|
| I-1 | 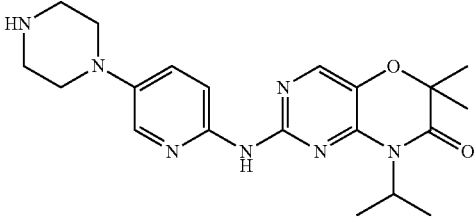 [SMILES: CC(C)N1C(=O)C(C)(C)Oc2cnc(Nc3ccc(N4CCNCC4)cn3)nc21] |
| I-2 | 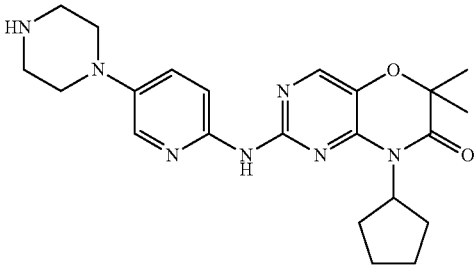 [SMILES: CC1(C)Oc2cnc(Nc3ccc(N4CCNCC4)cn3)nc2N(C2CCCC2)C1=O] |
| I-3 | 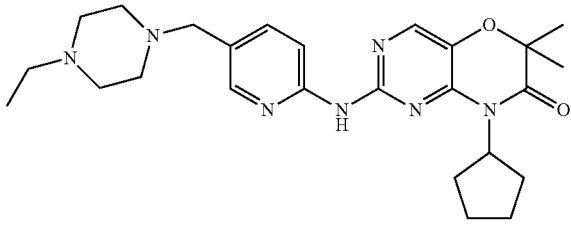 [SMILES: CCN1CCN(Cc2ccc(Nc3ncc4c(n3)N(C3CCCC3)C(=O)C(C)(C)O4)nc2)CC1] |
| I-4 | 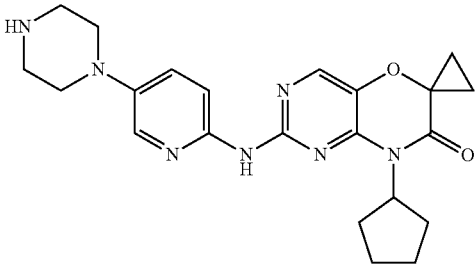 [SMILES: O=C1N(C2CCCC2)c2nc(Nc3ccc(N4CCNCC4)cn3)ncc2OC12CC2] |
| I-5 | 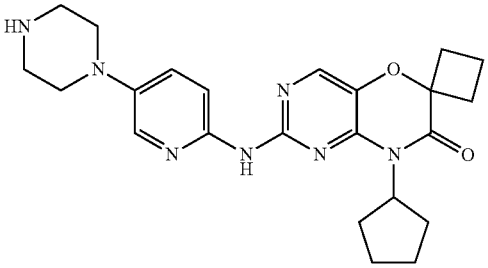 [SMILES: O=C1N(C2CCCC2)c2nc(Nc3ccc(N4CCNCC4)cn3)ncc2OC12CCC2] |

-continued
| Compound | Structure |
|---|---|
| I-6 | 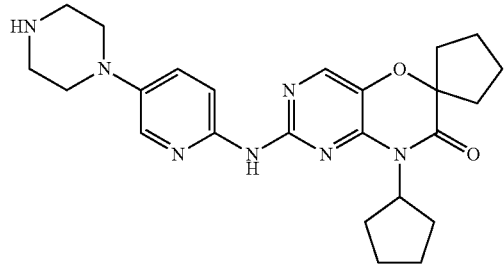 [SMILES: O=C1N(C2CCCC2)c2nc(Nc3ccc(N4CCNCC4)cn3)ncc2OC12CCCC2] |
| I-7 | 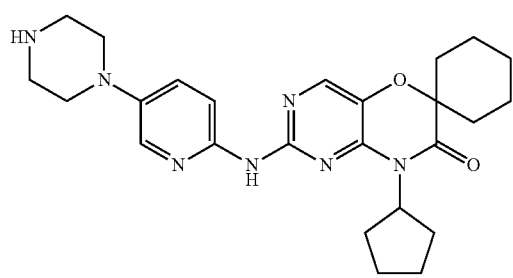 [SMILES: O=C1N(C2CCCC2)c2nc(Nc3ccc(N4CCNCC4)cn3)ncc2OC12CCCCC2] |
| I-8 | 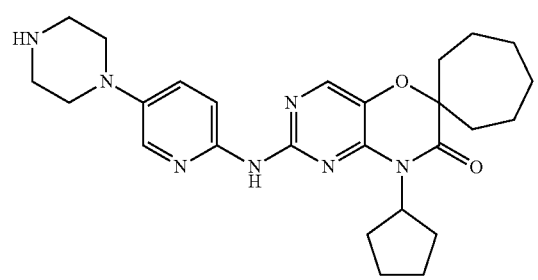 [SMILES: O=C1N(C2CCCC2)c2nc(Nc3ccc(N4CCNCC4)cn3)ncc2OC12CCCCCC2] |
| I-9 | 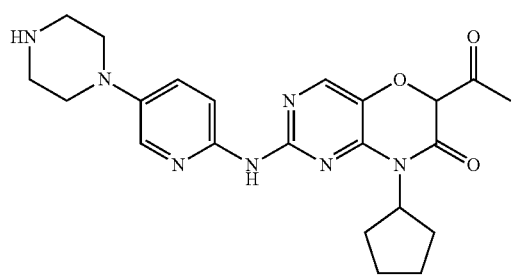 [SMILES: CC(=O)C1Oc2cnc(Nc3ccc(N4CCNCC4)cn3)nc2N(C2CCCC2)C1=O] |
| I-10 | 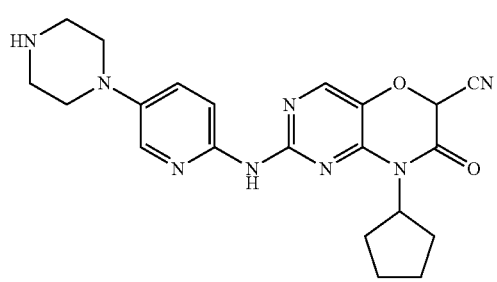 [SMILES: N#CC1Oc2cnc(Nc3ccc(N4CCNCC4)cn3)nc2N(C2CCCC2)C1=O] |

-continued
| Compound | Structure |
|---|---|
| I-11 | 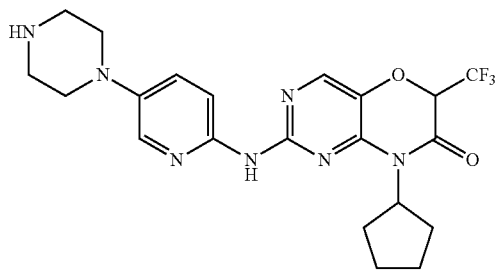 [SMILES: O=C1C(C(F)(F)F)Oc2cnc(Nc3ccc(N4CCNCC4)cn3)nc2N1C1CCCC1] |
| I-12 | 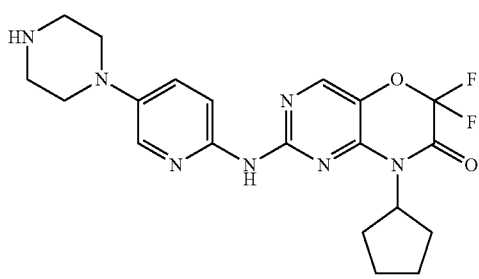 |
| I-13 | 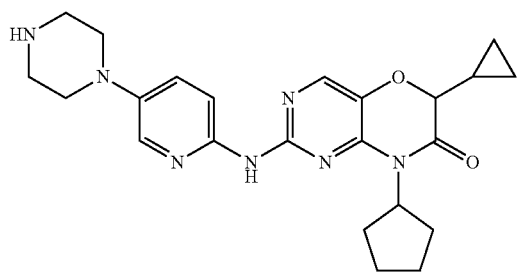 [SMILES: O=C1C(C2CC2)Oc2cnc(Nc3ccc(N4CCNCC4)cn3)nc2N1C1CCCC1] |
| I-14 | 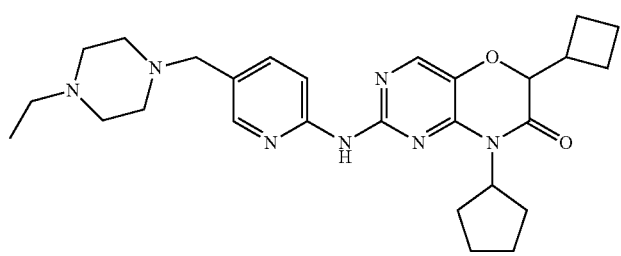 [SMILES: CCN1CCN(Cc2ccc(Nc3ncc4c(n3)N(C3CCCC3)C(=O)C(C3CCC3)O4)nc2)CC1] |
| I-15 | 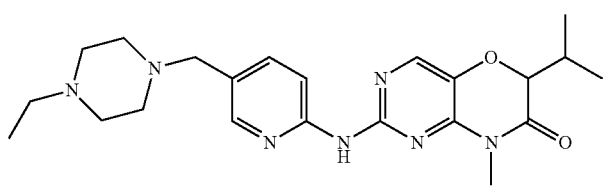 [SMILES: CCN1CCN(Cc2ccc(Nc3ncc4c(n3)N(C)C(=O)C(C(C)C)O4)nc2)CC1] |
| I-16 | 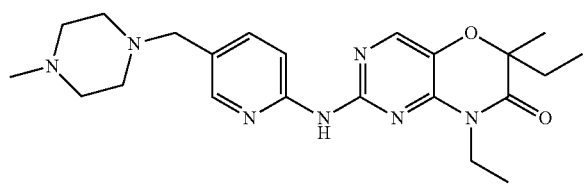 [SMILES: CCN1C(=O)C(C)(CC)Oc2cnc(Nc3ccc(CN4CCN(C)CC4)cn3)nc21] |

-continued
| Compound | Structure |
|---|---|
| I-18 | 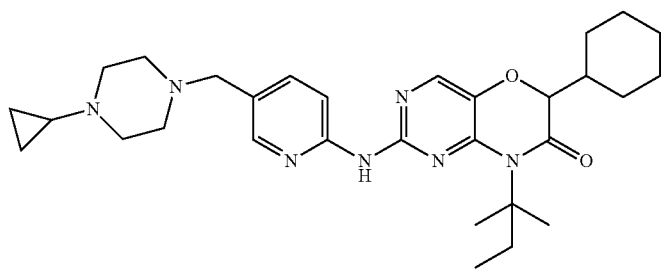 [SMILES: CCC(C)(C)N1C(=O)C(C2CCCCC2)Oc2cnc(Nc3ccc(CN4CCN(C5CC5)CC4)cn3)nc21] |
| I-20 | 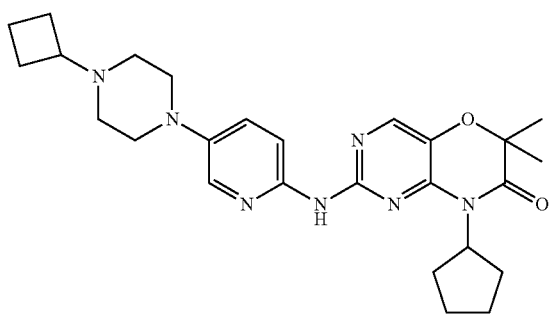 [SMILES: CC1(C)Oc2cnc(Nc3ccc(N4CCN(C5CCC5)CC4)cn3)nc2N(C2CCCC2)C1=O] |
| I-21 | 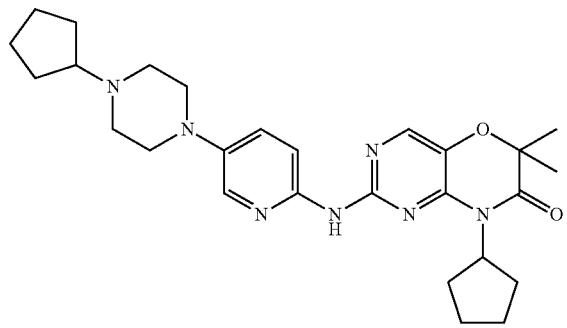 [SMILES: CC1(C)Oc2cnc(Nc3ccc(N4CCN(C5CCCC5)CC4)cn3)nc2N(C2CCCC2)C1=O] |
| I-22 | 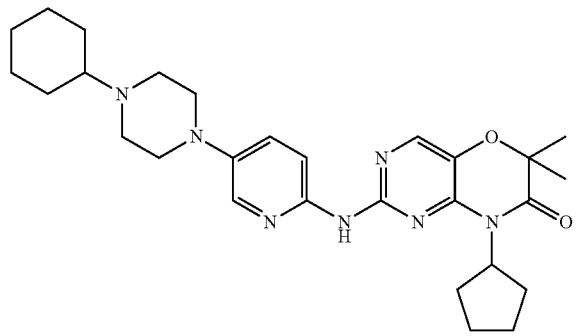 [SMILES: CC1(C)Oc2cnc(Nc3ccc(N4CCN(C5CCCCC5)CC4)cn3)nc2N(C2CCCC2)C1=O] |
| I-25 | 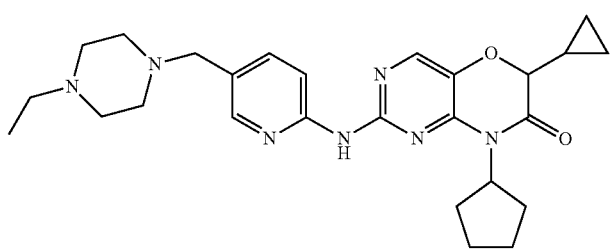 [SMILES: CCN1CCN(Cc2ccc(Nc3ncc4c(n3)N(C3CCCC3)C(=O)C(C3CC3)O4)nc2)CC1] |

-continued

| Compound | Structure |
|---|---|
| I-26 | 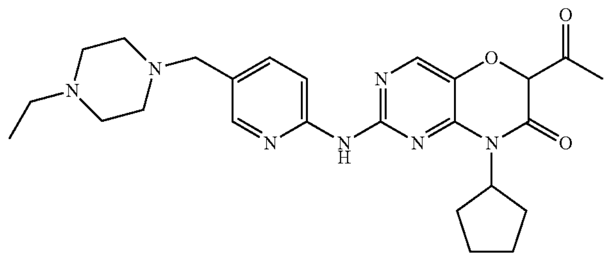 [SMILES: CCN1CCN(Cc2ccc(Nc3ncc4c(n3)N(C3CCCC3)C(=O)C(C(C)=O)O4)nc2)CC1] |
| I-27 | 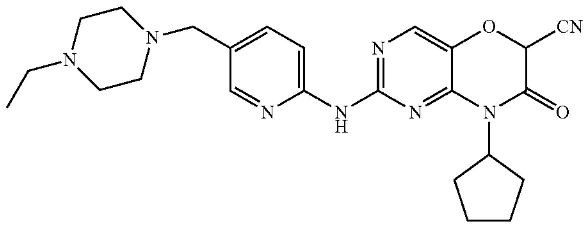 [SMILES: CCN1CCN(Cc2ccc(Nc3ncc4c(n3)N(C3CCCC3)C(=O)C(C#N)O4)nc2)CC1] |
| I-28 | 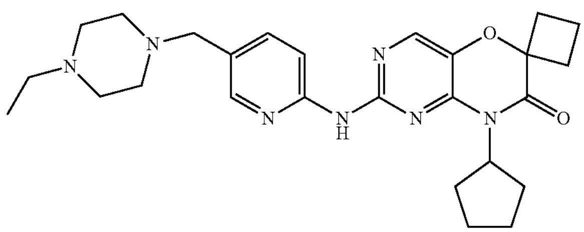 [SMILES: CCN1CCN(Cc2ccc(Nc3ncc4c(n3)N(C3CCCC3)C(=O)C3(CCC3)O4)nc2)CC1] |
| I-33 | 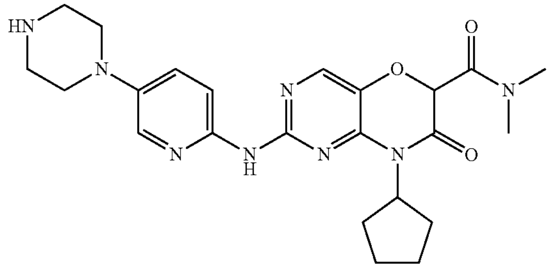 [SMILES: CN(C)C(=O)C1Oc2cnc(Nc3ccc(N4CCNCC4)cn3)nc2N(C2CCCC2)C1=O] |
| I-34 | 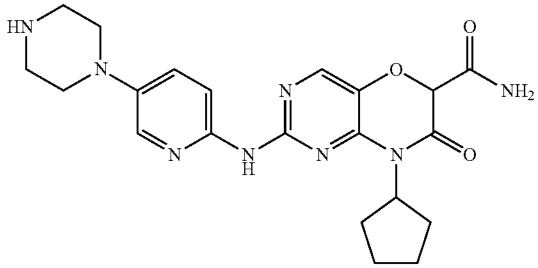 [SMILES: NC(=O)C1Oc2cnc(Nc3ccc(N4CCNCC4)cn3)nc2N(C2CCCC2)C1=O] |
| I-37 | 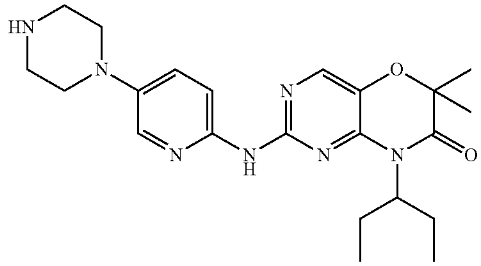 [SMILES: CCC(CC)N1C(=O)C(C)(C)Oc2cnc(Nc3ccc(N4CCNCC4)cn3)nc21] |

| Compound | Structure |
|---|---|
| I-38 | 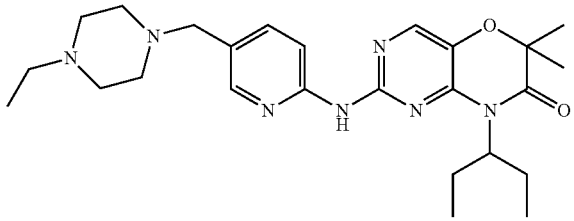 [SMILES: CCC(CC)N1C(=O)C(C)(C)Oc2cnc(Nc3ccc(CN4CCN(CC)CC4)cn3)nc21] |
or a pharmaceutically acceptable salt thereof.
5. A pharmaceutical composition comprising a therapeutically effective amount of the heterocyclic-substituted pyridinopyrimidinone derivative according to claim 1 and a pharmaceutically acceptable carrier or excipient.
* * * * *